(12) United States Patent
Archibong et al.

(10) Patent No.: US 12,343,365 B2
(45) Date of Patent: Jul. 1, 2025

(54) OKRA-DERIVED ANTIVIRAL COMPOSITION AND USES THEREOF

(71) Applicant: Meharry Medical College, Nashville, TN (US)

(72) Inventors: Anthony E. Archibong, Antioch, TN (US); Bindong Liu, Brentwood, TN (US); G. William Bates, Brentwood, TN (US); Elochukwu J. Ezekakpu, Nashville, TN (US); Lorin W. Simon, Antioch, TN (US); James E. K. Hildreth, Nashville, TN (US)

( * ) Notice: Subject to any disclaimer, the term of this patent is extended or adjusted under 35 U.S.C. 154(b) by 660 days.

(21) Appl. No.: 17/207,677

(22) Filed: Mar. 21, 2021

(65) Prior Publication Data

US 2021/0228664 A1    Jul. 29, 2021

Related U.S. Application Data

(63) Continuation of application No. PCT/US2019/051330, filed on Sep. 16, 2019.

(60) Provisional application No. 62/734,663, filed on Sep. 21, 2018.

(51) Int. Cl.
| | |
|---|---|
| *A61K 36/185* | (2006.01) |
| *A01N 1/02* | (2006.01) |
| *A61B 17/43* | (2006.01) |
| *A61K 9/00* | (2006.01) |
| *A61K 45/06* | (2006.01) |

(52) U.S. Cl.
CPC .......... *A61K 36/185* (2013.01); *A01N 1/0221* (2013.01); *A61B 17/43* (2013.01); *A61K 9/0014* (2013.01); *A61K 9/0019* (2013.01); *A61K 9/0036* (2013.01); *A61K 9/0053* (2013.01); *A61K 45/06* (2013.01); *A61K 2236/331* (2013.01); *A61K 2236/39* (2013.01); *A61K 2236/53* (2013.01)

(58) Field of Classification Search
None
See application file for complete search history.

(56) References Cited

FOREIGN PATENT DOCUMENTS

| | | |
|---|---|---|
| CN | 102688265 A | 9/2012 |
| CN | 105497572 A | 4/2016 |
| CN | 107050177 * | 8/2017 |
| EP | 1854812 B1 | 11/2007 |
| WO | 9317675 A1 | 9/1993 |
| WO | 2014043568 A1 | 3/2014 |
| WO | 2018/052848 A1 | 3/2018 |

OTHER PUBLICATIONS

Slam, M. "Phytochemical information and pharmacological activities of Okra (*Abelmoschus esculentus*): A literature-based review", Physiotherapy Research, vol. 33, No. 1, Oct. 22, 2018 (Oct. 22, 2018), pp. 72-80, KP055922170, GB ISSN: 0951-418X, DOI: 10.1002/ptr.6212.

Hisayoshi, T. et al. "Inhibition of HIV-1 Reverse Transcriptase Activity by Brasema schreberi (Junsai) Components", J. Biol. Macromol., vol. 14, No. 1, 2014, pp. 59-65, DOI: 10.14533/jom.14.59.

Dayal, B. et al. "Bioactive compounds in okra seed extract as novel anti-hepatitis C virus agents", 253rd ACS National Meeting & Exposition; Mar. 30-Apr. 7, 2017; San Francisco, Apr. 2, 2017 (Apr. 2, 2017).

Dayal, B. et al. "Okra seed phytochemicals: Application of 1-and 2 D NMR studies and their antiviral activity", 245th ACS National Meeting & Exposition; Apr. 10-11, 2013; New Orleans, Apr. 7, 2013 (Apr. 7, 2013).

Lengsfeld, C. et al. "Antiadhesive natural products for a new cytoprotective strategy against the early stages of infection by pathogens", Planta Medica, vol. 75, No. 9, Jul. 2009 (Jul. 2009), p. 888.

Messing J. et al.: "Antiadhesive Properties of *Abelmoschus esculentus* (Okra) Immature Fruit Extract against Helicobacter pylori Adhesion", Plos One, vol. 9, No. 1, Jan. 2014 (Jan. 2014), pp. 1-10, DOI: 10.1371/journal.pone.0084836.

Elkhalifa, Abd et al., "Development and Characterization of Novel Biopolymer Derived from *Abelmoschus esculentus* L. Extract and Its Antidiabetic Potential," Molecules, vol. 26, Jun. 2021, pp. 1-12.

Elkhalifa, Abd et al., "Okra (*Abelmoschus Esculentus*) as a Potential Dietary Medicine with Nutraceutical Importance for Sustainable Health Applications," Molecules, vol. 26, Jan. 2021, pp. 1-21.

Lengsfeld, C. "Glycosylated Compounds from Okra Inhibit Adhesion of Helicobacter pylori to Human Gastric Mucosa," Journal of Agricultual and Food Chemistry, vol. 52, Feb. 2004, pp. 1495-1503.

* cited by examiner

*Primary Examiner* — Michael V Meller
(74) *Attorney, Agent, or Firm* — Bradley Arant Boult Cummings LLP; Phil Walker; Jessica L. Zurlo

(57) ABSTRACT

Artificial cervical fluid is disclosed that contains a mucilaginous extract from the okra plant. The mucilaginous extract can be produced using a hot aqueous extractant or cold extraction process followed by separation of larger particles from the extract. The extract finds many uses, for example as a sperm storage medium, a sperm freezing medium, a sexual lubricant, an artificial insemination medium, an in vitro fertilization medium, and methods for treating and/or preventing infection, replication, and transmission of viruses, such as sexually transmitted viruses.

10 Claims, 14 Drawing Sheets

OKRA-DERIVED ANTIVIRAL COMPOSITION AND USES THEREOF

CROSS-REFERENCE TO RELATED APPLICATIONS

This application is a continuation of International Application No. PCT/US2019/051330, filed Sep. 16, 2019, which claims the benefit of U.S. Provisional Patent Application No. 62/734,663, filed Sep. 21, 2018, each of which is incorporated by reference herein in its entirety.

STATEMENT REGARDING FEDERALLY SPONSORED RESEARCH OR DEVELOPMENT

This invention was made with government support under grant numbers U54MD0007593 and 1P30AI110527 awarded by the U.S. National Institutes of Health. The government has certain rights in the invention.

In this context "government" refers to the government of the United States of America.

BACKGROUND

Cervical fluid (CF), sometimes referred to as cervical mucus, is produced by glands in the endocervix. Its properties change markedly at various points during the menstrual cycle, allowing it to function either as a barrier against the passage of material (such as spermatozoa and pathogenic organisms) through the cervix or as a selectively permeable barrier that can be penetrated by spermatozoa. Several hundred glands in the endocervix produce 20-60 mg of CF a day, increasing to 600 mg around the time of ovulation. The viscosity of CF varies, due in part to varying mucin concentrations. The viscosity and water content vary during the menstrual cycle; the CF is composed of around 93% water, reaching 98% at mid-cycle. It contains electrolytes such as calcium, sodium, and potassium; organic components such as glucose, amino acids, and soluble proteins; trace elements including zinc, copper, iron, manganese, and selenium; free fatty acids; enzymes such as amylase; and prostaglandins. Its consistency is determined by the influence of the hormones estrogen and progesterone. At midcycle around the time of ovulation—a period of high estrogen levels—the CF is thin to allow spermatozoa to enter the uterus, and is more alkaline and hence more hospitable to spermatozoa. It is also higher in electrolytes, which results in the "ferning" pattern that can be observed in drying CF under low magnification; as the CF dries, the salts crystallize, resembling the leaves of a fern. The CF has a stretchy character described as "Spinnbarkeit," most prominent around the time of ovulation.

At other stages of the cycle, the CF is thick and more acidic due to the effects of progesterone. This "infertile" CF acts as a barrier to spermatozoa thus preventing them from entering the uterus. Thick CF also prevents pathogens from interfering with a nascent pregnancy. A CF plug, called the operculum, forms inside the cervical canal during pregnancy. This provides a protective seal for the uterus against the entry of pathogens and against leakage of uterine fluids. The operculum is also known to have antibacterial properties. This plug is released as the cervix dilates, either during the first stage of childbirth or shortly before. It is visible as a blood-tinged mucous discharge.

CF has many potential practical uses. CF is used in sperm motility testing. The ability of CF to maintain the viability of spermatozoa indicates that it could be a useful storage or insemination medium. The selective permeability of CF indicates that it could be useful to separate spermatozoa from semen. As natural CF is difficult to collect in large volumes, and as CF with useful properties is only present at certain times during the menstrual cycle, there is a need in the art for an artificial CF with properties like those of CF that is present during ovulation.

SUMMARY

It has been unexpectedly discovered that a mucilaginous extract from the fruit of the okra plant (*A. esculentus*) can be produced with similar physical and biological properties to human CF, including the ability to be selectively penetrated by motile spermatozoa. This extract finds use for many of the same purposes as natural human CF, as further described below.

It has been unexpectedly discovered that an okra-derived composition can be produced with antiviral properties. This okra-derived composition finds use for many antiviral applications.

In a first aspect, a mucilaginous extract of the fruit of *A. esculentus* is provided, that is the product of the process comprising: (a) extracting a fruit of *A. esculentus* in an aqueous medium, to produce a first extract; and (b) separating a substantially clear mucilaginous fluid from the first extract; wherein the substantially clear mucilaginous fluid has properties similar to those of CF. Examples of such properties include: a Spinnbarkeit of at least about 10 cm when measured according to the test disclosed herein; displays ferning when subjected to the fern test; lacks visible green coloration; and when a semen sample is subjected to a sperm-mucus penetration test using the clear mucilaginous fluid in place of cervical mucus, spermatozoa that penetrate into the clear mucilaginous fluid have a significantly better indication of fertility than do spermatozoa in the semen sample.

In a second aspect, a storage medium for spermatozoa is provided, the medium comprising a mucilaginous extract of the fruit of *A. esculentus* and a multiplicity of spermatozoa.

In a third aspect, a method of sperm preservation is provided, comprising a freezing and storage medium comprising a mucilaginous extract of the fruit of *A. esculentus* and a multiplicity of spermatozoa.

In a fourth aspect, a coated condom is provided, comprising a condom in contact with a volume of a mucilaginous extract of the fruit of *A. esculentus* sufficient to at least partially coat the condom.

In a fifth aspect, a method of artificial insemination is provided, the method comprising inseminating a subject with a suspension of spermatozoa, the suspension comprising a mucilaginous extract of the fruit of *A. esculentus* and a multiplicity of spermatozoa suspended therein.

In a sixth aspect, a method of in vitro fertilization is provided, comprising: contacting a mixture of the extract of the first aspect and a plurality of spermatozoa with an unfertilized egg in vitro to create a fertilization mixture, incubating the fertilization mixture for a period of time sufficient for fertilization to occur and create an embryo, and transferring the embryo to the uterus of a subject.

In a seventh aspect, a method of providing artificial vaginal lubrication is provided, comprising applying a mucilaginous extract of the fruit of *A. esculentus* vaginally to a subject.

In an eighth aspect, a method of making a mucilaginous extract of the fruit of *A. esculentus* is provided, the method comprising extracting a fruit of *A. esculentus* in an aqueous medium, to produce a first extract; and separating a substantially clear mucilaginous fluid from the first extract.

In a ninth aspect, an apparatus for collecting viable spermatozoa is provided, the apparatus comprising a semen receptacle and a hollow elongate conduit connected to the semen receptacle, wherein the hollow elongate conduit is intended to contain the mucilaginous extract of the first aspect.

In a tenth aspect, a method of in vitro fertilization is provided, comprising: recovering viable spermatozoa from a semen sample into a mucilaginous extract of the fruit of *A. esculentus* with the apparatus described in the ninth aspect, contacting the viable spermatozoa with an unfertilized ovum in vitro to create a fertilization mixture, incubating the fertilization mixture for a period of time sufficient for fertilization to occur and create an embryo, and transferring the embryo to the uterus of a subject.

In an eleventh aspect, a method of treatment or prevention of HIV disease in a subject in need thereof is provided, the method comprising: administering to the subject a therapeutically effective amount of an okra-derived composition.

In a twelfth aspect, a method of decreasing the endocytosis of a virus into a eukaryotic cell is provided, the method comprising contacting the cell with an okra-derived composition in the presence of the virus.

In a thirteenth aspect, a method of decreasing replication of viral DNA in a eukaryotic cell infected by a virus is provided, the method comprising contacting said cell infected with said virus with an okra-derived composition.

In a fourteenth aspect, a method of preventing viral infection in a subject in need thereof is provided, the method comprising topically administering a therapeutically effective amount of an okra-derived composition to the subject at a site of anticipated viral infection.

In a fifteenth aspect, a method of reducing the likelihood of viral transmission in a sample of spermatozoa from a donor is provided, the method comprising (a) providing the sample from the donor, wherein said donor is infected with or at risk for infection of a sexually transmitted virus; and (b) introducing the sample to a storage medium comprising an okra-derived composition.

In a sixteenth aspect, a method of artificial insemination is provided, the method comprising inseminating a subject with a suspension of spermatozoa wherein said spermatozoa were obtained from a donor having or at risk for infection of a sexually transmitted virus, the suspension comprising an okra-derived composition and a multiplicity of spermatozoa.

In a seventeenth aspect, a method of isolating spermatozoa from semen obtained from a subject having or at risk for infection of a sexually transmitted virus while reducing the likelihood of transmission of said virus is provided, the method comprising (a) contacting a semen sample with a volume of an okra-derived composition; (b) allowing sufficient time for a multiplicity of spermatozoa in the semen sample to penetrate into the okra-derived composition to create a sperm suspension in the okra-derived composition; and (c) separating the sperm suspension from the semen sample.

In an eighteenth aspect, a pharmaceutical composition is provided, the pharmaceutical composition comprising a pharmaceutically acceptable carrier and an effective amount of an okra-derived composition sufficient to achieve a therapeutically effective concentration of the okra-derived composition at a site of viral infection.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 1A: placing the pinhole in the bottom of the centrifuge tube. FIGS. 1B-1C: collection of extract. FIG. 1D: measuring the Spinnbarkeit of the mucilaginous extract.

FIG. 5A shows the semen control (no mucilaginous extract). FIG. 5B shows the sample taken from the capillary containing mucilaginous extract.

FIG. 12A: placing the pinhole in the bottom of the centrifuge tube. FIGS. 12B-12C: collection of extract. FIG. 12D: measuring the Spinnbarkeit of the okra composition.

DETAILED DESCRIPTION

A. Definitions

Figure 1A:
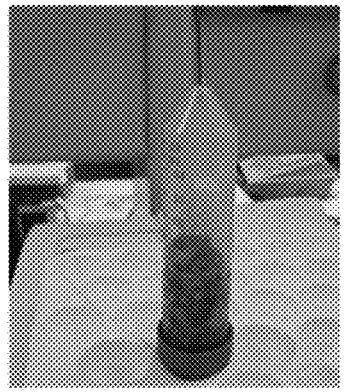
FIGS. 1A-1D: extraction of the okra fruits.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well-known functions or constructions may not be described in detail for brevity or clarity.

The terminology used herein is for the purpose of describing particular embodiments only and is not intended to be limiting. As used herein, the singular forms "a", "an," and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20%, preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

The terms "prevention," "prevent," "preventing," "suppression," "suppress," and "suppressing" as used herein refer to a course of action initiated prior to the onset of a clinical manifestation of a disease state or condition so as to reduce the likelihood or severity of such clinical manifestation of the disease state or condition. Such reduction of the likelihood or severity need not be absolute to be useful. The terms also refer to inhibiting the full development of a disease state or condition in a subject who is at risk of developing the disease state or condition.

The terms "treatment", "treat," and "treating" as used herein refer to a course of action initiated after the onset of a clinical manifestation of a disease state or condition so as to eliminate or reduce such clinical manifestation of the disease state or condition. Such treating need not be absolute to be useful.

The terms "in need of treatment" and "in need of prevention" as used herein refer to a judgment made by a caregiver that a patient requires or will benefit from treatment or prevention. This judgment is made based on a variety of factors that are in the realm of a caregiver's expertise, but that includes the knowledge that the patient is ill, or will be ill, as the result of a condition that is treatable by a method or composition of the present disclosure.

The term "individual," "subject," or "patient" as used herein refers to any animal, including mammals, such as mice, rats, other rodents, rabbits, dogs, cats, swine, cattle, sheep, horses, or primates, and humans. The term may specify male or female or both, or exclude male or female.

Terms such as "comprise" and "include" as used herein are inclusive, and non-exclusive, and should therefore be construed to mean "comprise/include but are not limited to." Permissive and optional terms such as "may" or "some embodiments" as used herein are also inclusive and non-exclusive.

The terms "inhibit," "decrease," and/or "reduce the likelihood of" (and like terms) generally refers to the act of reducing, either directly or indirectly, a function, activity, or behavior relative to the natural, expected, or average or relative to current conditions. It is understood that this is typically in relation to some standard or expected value, in other words, it is relative, but that it is not always necessary for the standard or relative value to be referred to. Such terms can include complete inhibition, complete reduction, or elimination of the likelihood of a function, activity, or behavior relative to the natural, expected, or average or relative to current conditions.

The term "pharmaceutically acceptable carrier" refers to one or more compatible solid or liquid fillers, diluents, or encapsulating substances that does not cause significant irritation to a human or other vertebrate animal and does not abrogate the biological activity and properties of the administered compound. Such carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

The term "therapeutically effective amount" as used herein refers to an amount of an agent, either alone or as a part of a pharmaceutical composition, that is capable of having any detectable, positive effect on any symptom, aspect, or characteristics of a disease state or condition. Such effect need not be absolute to be beneficial.

The terms "site susceptible to viral infection" and/or "site of anticipated viral infection" refer to any bodily site known to be a route for transmission of a virus and having cells competent to host the virus.

B. Okra-Derived Compositions and Methods of Making the Same

Okra-derived compositions are provided, that can be produced through aqueous extraction of the fruit of *A. esculentus* (referred to herein by its common name, okra), followed by the removal of at least a fraction of the particulate material in the resulting extract. In an embodiment of the okra-derived composition, an artificial CF is provided, made of a mucilaginous extract of the fruit of *A. esculentus* (referred to herein by its common name, okra). Like CF itself, the extract finds many uses related to fertility and sex, including such uses as a sexual lubricant, a sperm storage medium, a medium for assisted fertility procedures, a sperm penetration test medium, and an antibacterial agent. In other embodiments, the okra-derived composition finds uses related to treating and/or preventing infection and transmission of viruses, such as sexually transmitted viruses, and inhibiting replication of a virus.

In a general embodiment of the extract, it is the product of the process comprising: (a) extracting an okra fruit in an aqueous medium, to produce a first extract; and (b) separating a substantially clear mucilaginous fluid from the first extract. In this context "substantially clear" means that macroscopic (visible) particles have been removed from the extract. Some embodiments of the mucilaginous fluid are completely clear, meaning that the particulate fraction has been removed to the extent that the mucilaginous fluid does not appear cloudy to the unaided eye. Such removal may be achieved by any means known in the art. For example, a substantially clear mucilaginous fluid may be produced by straining the first extract through one or more pores of about 1 mm diameter or less. In a specific embodiment, the first extract is drained through a single pore of about 1 mm diameter under the force of gravity, which results in a substantially clear mucilaginous fluid. Other means include filtration, centrifugation, settling (with or without flocculants), and vortex separation.

The rate and efficiency of extraction may be improved by chopping the fruit into two or more pieces. In an exemplary embodiment the fruit is chopped into slices about 1-2 mm thick. Prior to any chopping steps, the seeds may be removed, or the ribs may be removed, or both (doing so has been observed to eliminate a greenish color in the extract that is otherwise present—although this color is not known to affect the properties of the extract).

The outer surface of the fruit may be sanitized prior to extraction to reduce the likelihood of microbial contamination of the extract. Such sanitation may be performed using chemical sanitizers, such as an ethanol solution (for example, 70% v/v ethanol in water). Ethanol has the advantage of low toxicity and high partial vapor pressure that results in rapid evaporation. Other chemical sanitizers could also be used. It is contemplated that other microbicidal agents could be used, such as gamma radiation or combined heat and pressure.

The extraction step may be carried out at an elevated temperature. For example, the extraction may be performed by boiling the fruit in the aqueous medium. Water (as from a municipal water supply) has been found to be particularly suitable for use when the fruit is boiled. Boiling has the advantage of completing the extraction at a rapid rate. Alternatively, extraction may be performed at a lower temperature. At such lower temperatures extraction may take longer than at a boiling temperature; however, lower temperature extraction has the advantage of producing an extract without the green color. For example, in a specific embodiment, extraction is performed at 4° C. for 4 hours.

Agitation may be used to increase the rate of extraction as well. Extraction at a lower temperature may also be performed with water, and it has also been found that lower temperature extraction may be performed with human tubal fluid (HTF) or HTF medium. HTF medium is a synthetic defined medium that is commercially available (for example, from Irvine Scientific, Santa Ana, California USA). Typically HTF medium is buffered against pH drift using a carbonate-$CO_2$ buffer system, in which case it is referred to in this disclosure as "bicarbonate buffered HTF medium." Other kinds of HTF media are available, for example, HEPES buffered HTF medium is available from Irvine Scientific, Santa Ana, California USA. In further embodiments, of the mucilaginous fluid the HTF may contain albumin, such as human serum albumin, to facilitate extraction. A specific embodiment of the aqueous extractant contains 0.5% w/v human serum albumin or bovine serum albumin. In still another embodiment, the extraction step may be performed with an antibiotic. For example, the fruit may be contacted with an aqueous medium including an antibiotic. Suitable antibiotics include, but are not limited to, penicillin, streptomycin, and combinations thereof. In one embodiment, the extraction step may be performed with an antibiotic in an amount of about 0.4 g/L to about 0.8 g/L. In another embodiment, the antibiotic may be used in an amount of about 0.5 g/L to about 0.7 g/L. For instance, the antibiotic may be used in an amount of about 0.5 g/L to about 0.6 g/L.

As described above, the okra composition is the product of an aqueous extraction step followed by coarse particle separation. The extraction and separation steps may employ any technique known in the art. For instance, the separation step may employ any technique for particle separation known in the art. Suitable separation techniques include, but are not limited to, extraction, evaporation, distillation, filtration, centrifugation, chromatography, drying, and/or freezing.

As stated above, the substantially clear mucilaginous fluid has properties similar to those of CF. Examples of such properties include: a Spinnbarkeit of at least about 10 cm when measured according to the test disclosed herein; displays ferning when subjected to the fern test; lacks visible green coloration; and when a semen sample is subjected to a sperm-mucus penetration test using the clear mucilaginous fluid in place of cervical mucus, sperm that penetrate into the clear mucilaginous fluid have a significantly better indication of fertility than do sperm in the semen sample. Each of these properties, on its own, confers significant utility to the mucilaginous fluid.

Spinnbarkeit is the elastic quality of a fluid, and it is specifically measured as a characteristic of mucus of the uterine cervix, especially shortly before ovulation. As is known in the art, the Spinnbarkeit of CF decreases shortly before ovulation. Functionally, this elastic quality contributes to the lubricating qualities of the mucilaginous fluid. It also presents a mechanical barrier to non-motile semen components, such as prostaglandins, which act as a selective barrier that admits spermatozoa but excludes other components. This property is advantageous in a medium for assisted reproduction procedures and as a medium for use in a sperm penetration test. Spinnbarkeit is measured by contacting the surface of the fluid with an object, such as a glass pipette or polypropylene centrifuge tube, and raising the object above the level of the fluid. A thread of adhered fluid will form, and the object is progressively raised until the thread breaks. Spinnbarkeit is thus measured as a distance. Some embodiments of the clear mucilaginous fluid have a Spinnbarkeit of at least about 10 cm. In further embodiments, the clear mucilaginous fluid has a Spinnbarkeit of at least about 15 cm.

The fern test detects solutes in CF, which crystalize as the fluid evaporates, forming microscopic structures reminiscent of the leaves of a fern on a stem that can be viewed under a low-power microscope. The fern test is often used to provide evidence of the presence of amniotic fluid in CF, and is used in obstetrics to detect rupture of membranes and onset of labor. Ferning is due to the presence of sodium chloride in the CF, which is frequently due to estrogen's effects in vivo. The artificial CF described herein under some conditions displays ferning when observed by the fern test. The ferning that has been observed indicates similar composition to the follicular phase of the menstrual cycle.

Spermatozoa that penetrate into certain embodiments of the clear mucilaginous fluid have a significantly better indication of fertility than do spermatozoa in the semen sample. These qualities can be measured using the cervical mucus penetration test (CMPT—also called the sperm penetration test). The CMPT is a widely used method known by those of ordinary skill in the art. As referred to in this disclosure, the CMPT is the standard protocol of Tang et al., *Human Reproduction* 14:2812-2817 (1999). All media used in this test must be pre-equilibrated to 37° C. Circular cross-section capillary tubes are recommended for use. Each tube is filled by aspiration using a 1 mL syringe and a plastic tube attached to the upper end of the capillary while the lower end is dipped into a pool of cervical mucus, mucilaginous extract, or other media. A column of medium is aspirated into the tube so that the upper meniscus is close but not at the top of the tube. Great care should be taken to avoid trapping air bubbles within the column. The top of the tube is then sealed with PLASTICINE and any trailing medium should be cut off the lower end to produce a flat interface. Approximately 100 µL of liquefied semen should be placed in the bottom of a small conical plastic tube and a capillary tube containing the cervical mucus or other media placed with its open end in the semen. Two semen reservoirs and capillary tubes will then be mounted on a microscope slide as shown in the WHO manual (World Health Organization (1999) *WHO Laboratory Manual for the Examination of Human Semen and Sperm-Cervical Mucus Interaction*; Cambridge University Press, Cambridge), following which, the slides are placed in a Petri dish containing damp sponges to maintain humidity and prevent drying of the semen and media. It is recommended that capillary tubes be incubated in the horizontal position for 60 minutes. Subsequently, the slides are removed from the Petri dishes and the capillary tube viewed under bright field illumination with a 20× phase-contrast objective lens and 10× oculars. The microscope stage should be adjusted to select a focal plane incorporating the central axis of the capillary and, at this magnification, the microscope field width approximates the inner diameter of the capillary tube. The length of the tube is then scanned to establish the distance furthest from the semen reservoir attained by spermatozoa.

In addition, the mucilaginous fluid may have one or more properties that are not necessarily present in human CF. For example, okra extracts have been observed to have anti-adhesive properties against certain microbes, specifically *Helicobacter pylori*. Consequently, it is contemplated that the mucilaginous fluid may have anti-adhesive properties against viruses and microorganisms.

The mucilaginous fluid provided herein serves as an effective substitute for CF in the CMPT, as it is selectively penetrated by spermatozoa with high viability. When a semen sample is subjected to a sperm-mucus penetration test using some embodiments of the clear mucilaginous fluid in place of cervical mucus, sperm that penetrate into the clear mucilaginous fluid have a significantly higher rate of normal morphology as compared to spermatozoa in the semen sample. When a semen sample is subjected to a sperm-mucus penetration test using further embodiments of the clear mucilaginous fluid in place of cervical mucus, sperm that penetrate into the clear mucilaginous fluid have a significantly higher rate of progressive motility as compared to spermatozoa in the semen sample. When a semen sample is subjected to a sperm-mucus penetration test using still further embodiments of the clear mucilaginous fluid in place of cervical mucus, sperm that penetrate into the clear mucilaginous fluid have a significantly higher grade of motility as compared to spermatozoa in the semen sample. In this context, the property is "significantly higher" if a person skilled in the art, such as a board-certified andrologist, would note that the property is markedly higher when using standard clinical tests.

Without wishing to be bound by any hypothetical model, it is believed that the mucilaginous extract contains four main polysaccharides and protein. The polysaccharides are dominated by rhamnose, galactose, and uronic acid monomers. Some embodiments of the extract comprise 7-28% mol/mol rhamnose, 12-50% mol/mol galactose, 14-56% mol/mol uronic acids, and 12-48% mol/mol protein (in which mole percent refers to the molarity of the specific fraction divided by the combined molarity of all sugar monomers, uronic acids, and proteins after hydrolysis of the polysaccharides). Further embodiments of the extract comprise one or more of 11.0-16.6% mol/mol rhamnose, 19.8-29.6% mol/mol galactose, 22.8-34.2% mol/mol uronic acids, and 19.0-28.4% mol/mol protein. Still further embodiments comprise one or more of 13.8% mol/mol rhamnose, 24.7% mol/mol galactose, 28.5% mol/mol uronic acids, and 23.7% mol/mol protein. Further embodiments of the extract further comprise one or more of 0.75-1.5% mol/mol arabinose, 0.4-1.2% mol/mol xylose, 0.45-1.8% mol/mol mannose, and 3.0-12% glucose. Still further embodiments of the extract may comprise one or more polysaccharides having any one of the structures shown in FIGS. 6A-D.

C. Cryopreservation Medium for Spermatozoa

The artificial CF described above finds use as cryopreservation medium for sperm. The cryopreservation medium comprises any embodiment of the artificial CF described above, and may further comprise a plurality of spermatozoa. The medium may also include any of several useful cryopreservative components, including one or more components such as glycerol, citrate, egg yolk, and antibacterial agents. Glycerol may be present at any concentration known in the art to preserve cellular viability upon freezing; examples of such concentrations include about 5-25% v/v, more specifically about 10-20% v/v, 12% v/v, and 15% v/v. Citrate and egg yolk can be used to reduce osmotic stress on the cells during penetration by glycerol. Antibiotics can be used to reduce the likelihood of microbial contamination of the sample. Such components may be used at concentrations that would be used in standard glycerol and glycerol-egg yolk cryopreservatives, in which the balance of the composition is the artificial CF.

The cryopreservative can be used in a method of sperm preservation. The method involves providing a composition comprising the cryopreservative in combination with a plurality of spermatozoa, and freezing the composition. In some embodiments of the method the composition is frozen at a temperature of about −10° C. or below; in further embodiments the composition is frozen at −40° C. or below; in still further embodiments the temperature is about −80°, −100°, −140°, −160°, −180°, or −190° C. or below. Any embodiment of the cryopreservative disclosed above may be used. The method may further comprise thawing the composition as needed.

D. Pharmaceutical Compositions

In one embodiment, the okra composition of the fruit of *A. esculentus* is in the form of compositions, such as but not limited to, pharmaceutical compositions. Pharmaceutical compositions are provided including one or more of the disclosed okra compositions, and optionally pharmaceutically acceptable diluents, preservatives, solubilizers, emulsifiers, adjuvants, excipients, and/or carriers.

To form a pharmaceutically acceptable composition suitable for administration, such compositions will contain a therapeutically effective amount of the okra composition. The disclosed compositions are administered to a subject in an amount sufficient to deliver a therapeutically effective amount of the okra composition so as to be effective in the treatment and prevention of the methods disclosed herein. The precise dosage may vary according to a variety of factors such as, but not limited to, the subject's condition, weight, sex, and age. In this aspect, the selected dosage depends upon the desired therapeutic effect, on the route of administration, and on the duration of the treatment desired. Generally, for intravenous injection or infusion, the dosage may be lower.

The pharmaceutical compositions may be formulated to achieve a desired concentration of the okra composition at a site of viral infection. For example, the disclosed pharmaceutical compositions may be formulated to achieve desired concentrations at one or more sites susceptible to viral infection including, but not limited to, dendritic cells, T cells, such as CD4+ T cells, vaginal epithelial cells, cervical epithelial cells, uterine epithelial cells, and rectal epithelial cells. In one embodiment, the composition includes an effective amount of okra composition sufficient to achieve a therapeutically effective concentration of about 3.25 percent to about 15 percent V/V of the okra composition at one or more sites susceptible to viral infection, for example, dendritic cells, T cells, such as CD4+ T cells, vaginal epithelial cells, cervical epithelial cells, uterine epithelial cells, and rectal epithelial cells. In another embodiment, the composition includes an effective amount of okra composition sufficient to achieve a therapeutically effective concentration of about 5 percent to about 10 percent V/V of the okra composition at one or more sites susceptible to viral infection.

The pharmaceutical compositions may be formulated to be provided to the subject in any method known in the art. For instance, the pharmaceutical compositions may be formulated for administration by parenteral (for example, intramuscular, intraperitoneal, intravitreally, intravenous (IV), or subcutaneous injection), enteral, transmucosal (for example, nasal, vaginal, rectal, or sublingual), or transdermal routes of administration and can be formulated in dosage forms appropriate for each route of administration. The disclosed compositions may be formulated to be administered only once to the subject or more than once to the subject. Furthermore, when the compositions are administered to the subject more than once, a variety of regimens may be used, such as, but not limited to, once per day, once per week, once per month, or once per year. The compositions may also be formulated to be administered to the subject more than one time per day. The therapeutically effective amount of the okra composition and appropriate dosing regimens may be identified by routine testing in order to obtain optimal activity, while minimizing any potential side effects. In addition, formulation for co-administration or sequential administration of other agents may be desirable.

In certain embodiments, the disclosed compositions may be formulated to be administered systemically, such as by intravenous administration, or locally such as by subcutaneous injection. Typically, local administration causes an increased localized concentration of the composition which is greater than that which can be achieved by systemic administration.

The disclosed compositions may further include agents which improve the solubility, half-life, absorption, etc. of the okra composition. Furthermore, the disclosed compositions may further include agents that attenuate undesirable side effects and/or decrease the toxicity of the okra composition. Examples of such agents are described in a variety of texts, such as, but not limited to, Remington: The Science and Practice of Pharmacy (20th Ed., Lippincott, Williams & Wilkins, Daniel Limmer, editor).

1. Formulations for Parenteral Administration

The disclosed compositions may be formulated for parenteral administration, for example, intramuscular, intraperitoneal, intravenous, or subcutaneous administration. In some embodiments, the compositions disclosed herein are formulated for parenteral injection, for example, in an aqueous solution. The formulation may also be in the form of a suspension or emulsion. The disclosed compositions may optionally include one or more of the following for parenteral administration: diluents, sterile water, buffered saline of various buffer content (for example, Tris-HCl, acetate, phosphate), pH and ionic strength, ionic liquids, and HPBCD; and additives such as detergents and solubilizing agents (for example, TWEEN®20 (polysorbate-20), TWEEN®80 (polysorbate-80)), anti-oxidants (for example, ascorbic acid, sodium metabisulfite), and preservatives (for example, Thimersol, benzyl alcohol) and bulking substances (for example, lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

In some embodiments, the disclosed compositions are formulated for enteral administration including oral, sublingual, and rectal delivery. In one embodiment, the disclosed compositions are administered in solid dosage form. Suitable solid dosage forms include tablets, capsules, pills, lozenges, cachets, pellets, powders, granules, or incorporation of the material into particulate preparations of polymeric compounds such as polylactic acid, polyglycolic acid, or into liposomes. In another embodiment, the disclosed compositions are administered in liquid dosage form. Examples of liquid dosage forms for enteral administration include pharmaceutically acceptable emulsions, solutions, suspensions, and syrups, which may contain other components including inert diluents; preservatives; binders; stabilizers; adjuvants such as wetting agents, emulsifying and suspending agents; and sweetening, flavoring, and perfuming agents.

Controlled release oral formulations, for example, delayed-release or extended-release formulations, may also be desirable. For example, the disclosed compounds may be encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings (for example, delayed-release or extended-release coatings) prior to incorporation into the finished dosage form. In still another embodiment, the disclosed compounds may be dispersed in a matrix material, which gels or emulsifies upon contact with an aqueous medium.

Such matrices may be formulated as tablets or as fill materials for hard and soft capsules.

For enteral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance, a coating impermeable to at least pH 5.0 is essential. Examples of common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

In some embodiments, the disclosed compositions are formulated for topical application. Topical dosage forms including, but not limited to, lotions, sprays, ointments, creams, pastes, lubricants, and emulsions, containing the okra composition, can be admixed with penetration enhancers and a variety of carrier materials well known in the art, such as alcohols, aloe vera gel, allantoin, glycerine, vitamin A and E oils, mineral oil, PPG2 (polypropylene glycol 2) myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage, or dressing for transdermal delivery, or may be applied to a bandage or dressing for delivery directly to the site of a wound or cutaneous injury.

4. Formulations for Transmucosal Administration

In some embodiments, the disclosed compositions may be formulated for transmucosal administration. Transmucosal administration refers to a route of administration in which the drug is diffused through the mucous membrane. For instance, the disclosed compositions may be formulated for inhalation, nasal, oral (sublingual, buccal), vaginal, rectal, or ocular routes. Formulations for administration to the mucosa will typically be spray-dried drug particles, which may be incorporated into, for example, a tablet, gel, capsule, suspension, emulsion, cream, foam, ointment, tampon, enema solution, or suppository.

E. Methods of Use

Various methods of using the extract and the cryopreservation medium are provided.

One such method is a method of assisted fertility using any embodiment of the extract or storage medium described above combined with a plurality of spermatozoa. A first general embodiment of the method of assisted fertility is an in vitro fertilization method, comprising contacting a mixture of any embodiment of the extract or storage medium described above and a plurality of spermatozoa with an unfertilized egg in vitro to create a fertilization mixture, incubating the fertilization mixture for a period of time sufficient for fertilization to occur and create an embryo, and transferring the embryo to the uterus of a subject. Any variants of in vitro fertilization that are known in the art may be used. A second general embodiment is a method of artificial insemination comprising providing a mixture of a plurality of spermatozoa with any embodiment of the extract or storage medium described above, and placing the mixture into the uterus of a subject. Any variants of artificial insemination that are known in the art may be used.

Another general embodiment of a method of assisted fertility comprises recovering viable spermatozoa from semen into the mucilaginous extract of the fruit of *A. esculentus* with the apparatus described below, contacting the spermatozoa to an unfertilized egg in vitro to create a fertilization mixture, incubating the fertilization mixture for a period of time sufficient for fertilization to occur and create an embryo, and transferring the embryo to the uterus of a subject. The method may also comprise separating the extract from the spermatozoa, for example by centrifugal washing.

Another such method is a method of providing vaginal lubrication comprising applying any embodiment of the extract described above to a subject. Additional components may include additional lubricants (such as glycerin and cellulose ether), gelling agents, moisturizers (such as carrageenan), flavorings, fragrances, microbicides, spermicides, and antivirals. Some embodiments of the method may be intended to provide lubrication that does not impair fertility, in which case the spermicide would be specifically omitted. The extract is applied to the genitalia of the subject, whether directly or on an intervening structure such as a condom. For example, the extract may be applied vaginally or phallically.

In another embodiment, the okra composition and pharmaceutical compositions described herein can be used, for example, to treat and/or prevent infection and transmission of viruses, such as sexually transmitted viruses.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art.

Figure 11:
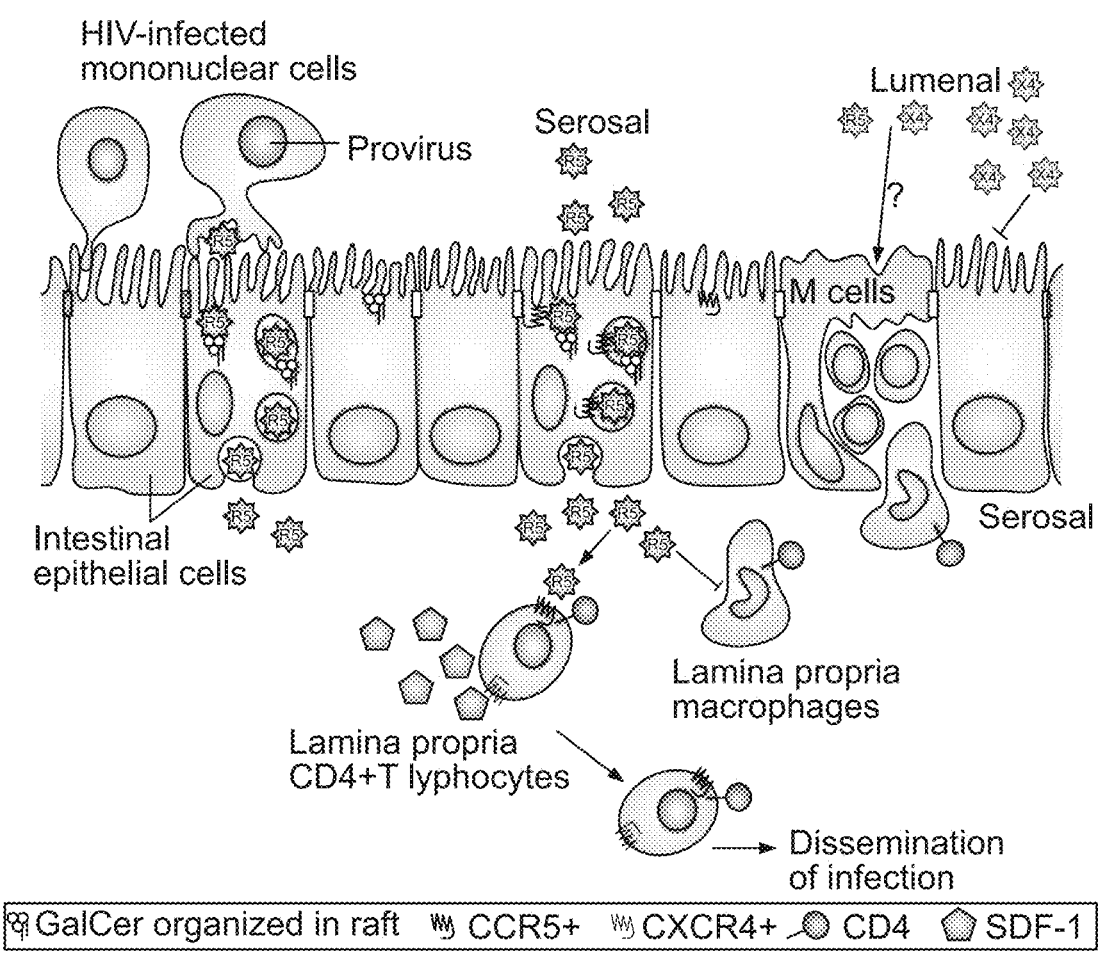
FIG. 11: schematic diagram showing at least one mechanism by which HIV-1 passes through the vaginal epithelium.

The okra composition disclosed herein has been found to inhibit viral transmission and replication, such as HIV replication. The human vaginal epithelium is the first line of defense against HIV-1 sexual transmission. It is believed that HIV-1 may enter the epithelial cells through endocytosis and accumulate inside of the cells (as shown in FIG. 11). The intracellular HIV particles then get released to the exterior of the cells through the endosomal recycling pathway. Without being bound by any particular theory, it is believed that the okra composition blocks HIV-1 transcytosis through vaginal epithelial cells and inhibits viral transmission and replication.

In one embodiment, the present disclosure provides for a method of decreasing endocytosis of a virus into a cell, the method including contacting the cell with the okra composition described herein in the presence of the virus. The cell may be a eukaryotic cell such as an epithelial cell. Examples of eukaryotic cells include, but are not limited to, a blood cell, dendritic cell, T cell, such as CD4+ T cell, vaginal epithelial cell, cervical epithelial cell, uterine epithelial cell, and rectal epithelial cell. In one embodiment, the method involves contacting a vaginal epithelial cell with the okra composition in the presence of the virus. Contact of a cell with the okra composition may result in a decrease of endocytosis of a virus into the cell by 5%, 10%, 20%, 30%, 40%, 50%, 60%, 70%, 80%, 90%, 95%, or at least any of the foregoing.

In another embodiment, the present disclosure provides for a method of treatment and/or prevention of infection and/or transmission of a virus in a subject in need thereof, the method including administering the okra composition or pharmaceutical compositions described herein to the subject in a therapeutically effective amount. Viruses that can be prevented or treated by the disclosed compositions include sexually transmitted viruses. Sexually transmitted viruses that may be prevented or treated by the disclosed compositions include, but are not limited to, human immunodeficiency virus (HIV), such as human immunodeficiency virus type I (HIV-I) and human immunodeficiency virus type II (HIV-II), herpes simplex viruses (HSV), human papillomavirus (HPV), hepatitis B virus (HBV), and cytomegalovirus. The method may also be useful for treatment and/or prevention of a disease and/or condition caused by the virus. For example, diseases and/or conditions that can be prevented or treated by the disclosed compositions include, but are not limited to, acquired immune deficiency syndrome (AIDS), HBV, and HCV.

In one embodiment, the disclosed okra composition or pharmaceutical compositions are used to treat or prevent infection and transmission of HIV. In this aspect, a further embodiment of the method includes co-administering an anti-HIV therapy to the subject. An anti-HIV therapy, as used herein, is any therapeutic that is useful for reducing viral load, preventing viral infection, prolonging the asymptotic phase of HIV infection, prolonging the life of a subject infected with HIV, or providing a therapeutic effect to a subject infected with HIV such as treating, inhibiting, preventing, reducing the severity of, or alleviating one or more symptoms associated with HIV. Anti-HIV therapies include, but are not limited to, nucleoside reverse transcriptase inhibitors (NRTIs) such as abacavir, emtricitabine, lamivudine, tenofovir disoproxil fumarate, and zidovudie; non-nucleoside reverse transcriptase inhibitors (NNRTIs) such as efavirenz, etravirine, nevirapine, and rilpivirine; inhibitors of HIV replication, such as protease inhibitors, e.g., atazanavir, darunavir, fosamprenavir, ritonavir, saquinavir, and tipranavir; fusion inhibitors such as enfuvirtide; CCR5 antagonists such as maraviroc; integrase inhibitors such as dolutegravir and raltegravir; post-attachment inhibitors such as ibalizumab; pharmacokinetic enhancers such as cobicistat; combination HIV medicines such as (i) abacavir and lamivudine, (ii) abacavir, dolutegravir, and lamivudine, (iii) abacavir, lamivudine, and zidovudine, (iv) atazanavir and cobicistat, (v) bictegravir, emtricitabine, and tenofovir alafenamide, (vi) darunavir and cobicistat, (vii) dolutegravir and rilpivirine, (viii) efavirenz, emtricitabine, and tenofovir disoproxil fumarate, (ix) efavirenz, lamivudine, and tenofovir disoproxil fumarate, (x) elvitegravir, cobicistat, emtricitabine, and tenofovir alafenamide fumarate, (xi) elvitegravir, cobicistat, emtricitabine, and tenofovir disoproxil fumarate, (xii) emtricitabine, rilpivirine, and tenofovir alafenamide, (xiii) emtricitabine, rilpivirine, and tenofovir disoproxil fumarate, (xiv) emtricitabine and tenofovir alafenamide, (xv) emtricitabine and tenofovir disoproxil fumarate, (xvi) lamivudine and tenofovir disoproxil fumarate, (xvii) lamivudine and zidovudine, and (xviii) lopinavir and ritonavir; cytokines; and chemokines.

In another embodiment, the okra composition or pharmaceutical compositions are used to treat or prevent infection and transmission of HBV. In this aspect, a further embodiment of the method includes co-administering an anti-HBV therapy to the subject. An anti-HBV therapy, as used herein, is any therapeutic that is useful for reducing viral load, preventing viral infection, prolonging the life of a subject infected with HBV, or providing a therapeutic effect to a subject infected with HBV such as treating, inhibiting, preventing, reducing the severity of, or alleviating one or more symptoms associated with HBV. Anti-HBV therapies include, but are not limited to, entecavir, lamivudine, adefovir dipivoxil, interferon alpha-2b, pegylated interferon, telbivudine, tenofovir alafenamide, and tenofovir.

The method of treatment and/or prevention includes administering to the subject the okra composition or pharmaceutical compositions in an amount sufficient to treat or prevent viral infection, for example, infection of a sexually transmitted virus. The method will often further include identifying a subject in need of such treatment or prevention. In another embodiment, the method includes delivering the okra composition or pharmaceutical composition to a site of infection in the subject. For instance, the method may include topically administering a therapeutically effective amount of the okra composition or pharmaceutical composition to the subject at a site of anticipated viral infection. Sites of infection of a virus may include, but are not limited to, dendritic cells, T cells, such as CD4+ T cells, vaginal epithelial cells, cervical epithelial cells, uterine epithelial cells, and rectal epithelial cells. In still another embodiment, when the subject is infected or suspected to be infected with HIV, the method may include delivering the okra composition or pharmaceutical composition to an HIV-competent host cell of the subject.

If, after the administration of the okra composition or pharmaceutical composition, the subject is still infected with the virus, then an optional step of the method is to continue administration of the okra composition or pharmaceutical composition.

In another embodiment, the present disclosure relates to a method for preventing or inhibiting replication of any one or more of the viruses disclosed above. For example, the present disclosure provides for a method of decreasing replication of viral DNA in a eukaryotic cell infected by a virus, the method including contacting the cell infected with the virus with the okra composition described herein. In still another embodiment, the method includes administering the okra composition or pharmaceutical compositions to the subject in a therapeutically effective amount to inhibit viral replication. For example, the method may include administering the okra composition or pharmaceutical compositions to a subject infected with HIV in a therapeutically effective amount such that viral replication of the HIV is inhibited. The okra composition can act as an agent for inhibiting replication of the virus.

The disclosed compositions can be administered to a subject in need thereof in combination or alternation with other therapies and therapeutic agents. In some embodiments, the disclosed compositions and the additional therapeutic agent are administered separately, but simultaneously, or in alternation. The disclosed compositions and the additional therapeutic agent can also be administered as part of the same composition. In other embodiments, the disclosed compositions and the second therapeutic agent are administered separately and at different times, but as part of the same treatment regimen.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6, 7, 14, 21, 28, 35, or 48 days prior to a first administration of second agent. The disclosed compositions can be the first or the second therapeutic agent.

The disclosed compositions and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules that may be administered with the disclosed compositions include, but are not limited to, cytokines, chemotherapeutic agents, radionuclides, other immunotherapeutics, enzymes, antimicrobials, antibiotics, antifungals, antivirals, anti-HIV therapies including, but not limited to, nucleoside reverse transcriptase inhibitors (NRTIs) such as abacavir, emtricitabine, lamivudine, tenofovir disoproxil fumarate, and zidovudie, non-nucleoside reverse transcriptase inhibitors (NNRTIs) such as efavirenz, etravirine, nevirapine, and rilpivirine, inhibitors of HIV replication, such as protease inhibitors, e.g., atazanavir, darunavir, fosamprenavir, ritonavir, saquinavir, and tipranavir, fusion inhibitors such as enfuvirtide, CCR5 antagonists such as maraviroc, integrase inhibitors such as dolutegravir and raltegravir, post-attachment inhibitors such as ibalizumab, pharmacokinetic enhancers such as cobicistat, combination HIV medicines such as (i) abacavir and lamivudine, (ii) abacavir, dolutegravir, and lamivudine, (iii) abacavir, lamivudine, and zidovudine, (iv) atazanavir and cobicistat, (v) bictegravir, emtricitabine, and tenofovir alafenamide, (vi) darunavir and cobicistat, (vii) dolutegravir and rilpivirine, (viii) efavirenz, emtricitabine, and tenofovir disoproxil fumarate, (ix) efavirenz, lamivudine, and tenofovir disoproxil fumarate, (x) elvitegravir, cobicistat, emtricitabine, and tenofovir alafenamide fumarate, (xi) elvitegravir, cobicistat, emtricitabine, and tenofovir disoproxil fumarate, (xii) emtricitabine, rilpivirine, and tenofovir alafenamide, (xiii) emtricitabine, rilpivirine, and tenofovir disoproxil fumarate, (xiv) emtricitabine and tenofovir alafenamide, (xv) emtricitabine and tenofovir disoproxil fumarate, (xvi) lamivudine and tenofovir disoproxil fumarate, (xvii) lamivudine and zidovudine, and (xviii) lopinavir and ritonavir, chemokines, anti-HBV therapies including, but not limited to, entecavir, lamivudine, adefovir dipivoxil, interferon alpha-2b, pegylated interferon, telbivudine, tenofovir alafenamide, and tenofovir, anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatoiregands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the disclosed compositions can be co-administered with one or more additional agents that function to enhance or promote an immune response.

Due to the ability of the mucilaginous okra extract to reduce the likelihood of transmission of viruses, such as sexually transmitted viruses, the okra composition may also be used as a blocking agent to prevent a virus from penetrating cervical and uterine epithelium during intrauterine insemination. For instance, the present disclosure provides for a method of reducing the likelihood of viral transmission in a sample of spermatozoa from a donor, the method including providing the sample from the donor, wherein said donor is infected with or at risk for infection of any of the sexually transmitted viruses discussed above and introducing the sample to any of the storage media described above, for example, the cryopreservation medium, including the okra composition. In another embodiment, the present disclosure provides for a method of artificial insemination, the method including inseminating a subject with a suspension of spermatozoa wherein said spermatozoa were obtained from a donor having or at risk for infection of any of the sexually transmitted viruses described above, the suspension including the okra composition and a multiplicity of spermatozoa. In still another embodiment, the present disclosure provides for a method of isolating spermatozoa from semen obtained from a subject having or at risk for infection of any of the sexually transmitted viruses described above while reducing the likelihood of transmission of said virus, the method including contacting a semen sample with a volume of the okra composition; allowing sufficient time for a multiplicity of spermatozoa in the semen sample to penetrate into the okra composition to create a sperm suspension in the okra composition; and separating the sperm suspension from the semen sample.

F. Sperm Penetration Test and Kit

A test is provided for measuring the motility of spermatozoa by measuring their ability to penetrate okra mucilage. The test comprises contacting a semen sample to a volume of mucilaginous okra extract, incubating the sample at about physiological temperature for a period of time, and measuring the distance of a leading spermatozoon from a location at which the semen sample was introduced. The test may be conducted on a glass surface, such as the surface formed by the interface of a glass slide and a coverslip. A path or "track" may be formed to corral the spermatozoa, enhancing the ease of measuring the distance traveled by the phalanxes. Incubation conditions may be any that are typically used during sperm motility tests; in a specific embodiment, incubation is conducted at 37° C. under a 5% v/v mixture of $CO_2$ in air. The semen sample can be classified as of normal motility or subnormal motility based on a benchmark distance. The benchmark distance may be established by the use of a control sample at the time of the test, or a previously established standard benchmark may be used. The classification of the semen sample may be made pursuant to a statistical test that incorporates a measure of central tendency and a measure of variation; such tests include Student's t-test, an ANOVA, and a confidence limit.

G. Coated Condom

A coated condom is provided comprising a condom in contact with a volume of any embodiment of the extract described above, the volume being sufficient to at least partially coat the condom. Some embodiments of the condom are entirely coated by the extract. A further embodiment of the condom is at least coated with the extract on its exterior surface. The condom may be constructed of any material known as suitable in the art, for example, latex, polyurethane, polyisoprene, lamb intestine, and nitrile rubber.

In some embodiments of the condom, the condom is coated by any embodiment of the vaginal lubricant described above.

H. Apparatus for Collecting Viable Spermatozoa

An apparatus for collecting viable spermatozoa is provided, the apparatus comprising a semen receptacle and a hollow elongate conduit connected to, or in fluid communication with, the semen receptacle, wherein the hollow elongate conduit is intended to contain any embodiment of the extract described above. A sample containing a plurality of spermatozoa is placed in the semen receptacle, and allowed to remain in contact with the extract for a period sufficient to allow motile spermatozoa to penetrate the extract. As explained in more detail in the example below, the extract has been observed to be selectively permeable to morphologically normal and motile spermatozoa.

Some embodiments of the apparatus comprise a valve positioned to reversibly close an end of the hollow elongate conduit against the passage of spermatozoa. Some embodiments of the valve prevent the passage of any particles, creating a watertight seal when closed. Further embodiments of the valve are configured to prevent the passage of particles above a certain effective diameter. A collection vessel may be positioned to receive material from the valve (when open).

I. Example 1: Method of Making Mucilaginous Extract

Figure 1B:
Figure 1C:
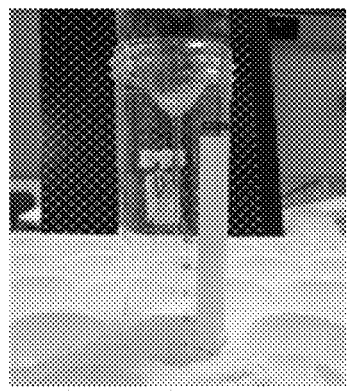

An 8"×8" aluminum foil sheet was sterilized with 70% ethanol and wiped dry with a task wipe, such as KIM-WIPES. Six okra fruits were thoroughly washed with a mild soap solution prior to being thoroughly rinsed with tap water (5×500 mL) followed by DI water (1×500 mL), and sterile wiped with a task wipe pre-soaked in 70% ethanol. After allowing ethanol film on okra fruits to dry (15-20 min), the fruits were placed on the sterile aluminum foil and okra slices (1-2 mm) were prepared with a sterile scalpel blade. Ten grams of sliced okra fruit portions were placed in each of three 50 mL centrifuge tubes containing 15, 20, or 25 mL of HTF-bicarbonate solution (25 mM of $Na_2CO_3$ in buffered human tubal fluid [HTF] containing 0.5% human serum albumin). Extraction tubes were rocked at 4° C. on a tissue rocker/shaker for 4 hours. Each extraction centrifuge tube was inverted and the bottom was sterilized with a 70% ethanol wipe. Using a pre-heated 18G needle, a pinhole was created at the center of the bottom of the tube with a pore size of approximately 1.0 mm (large enough to permit fluid escape but small enough to prevent okra seeds escape—FIG. 1A). Each extraction tube was inverted (cap side up) over another uncapped 50 mL centrifuge tube (FIG. 1B). The cap to the extraction tube was loosened to permit the clear extracted okra mucus to drip under gravitational force into the collection tube (FIG. 1C). The extracted mucus was clear and devoid of chlorophyll pigment.

Figure 1D:
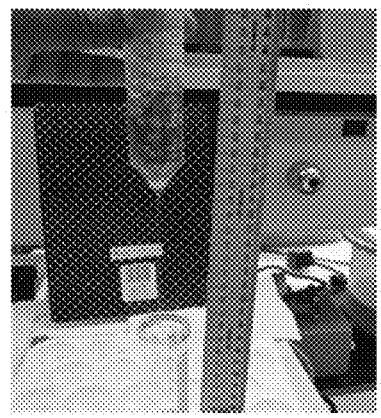
Figure 2A:
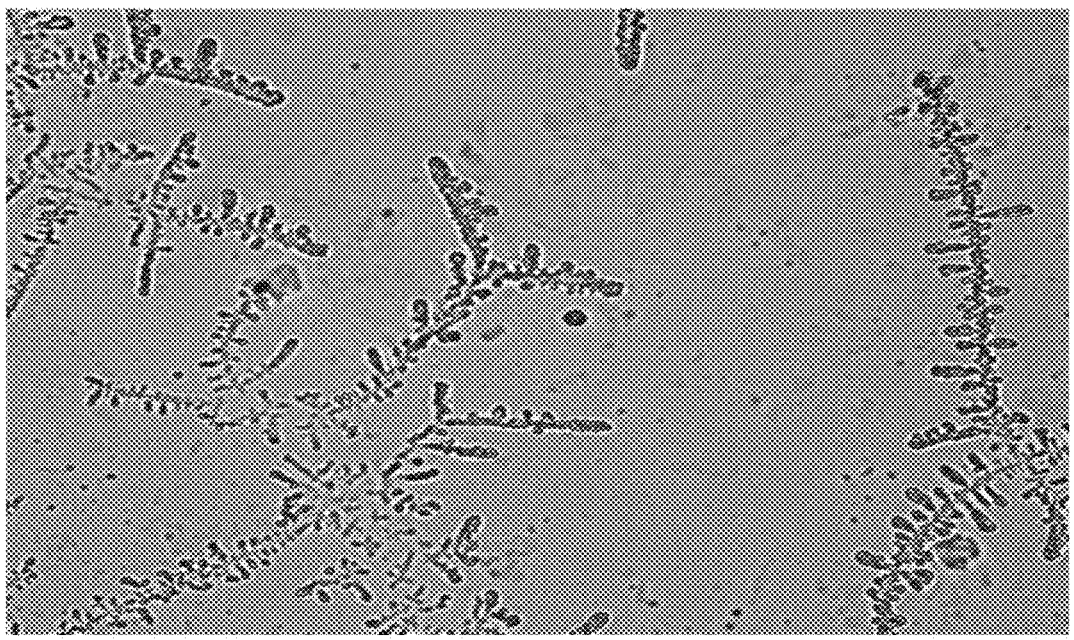
FIGS. 2A-2B: comparison of the ferning patterns of human cervical mucus (FIG. 2A) and the mucilaginous extract (FIG. 2B).
Figure 2B:
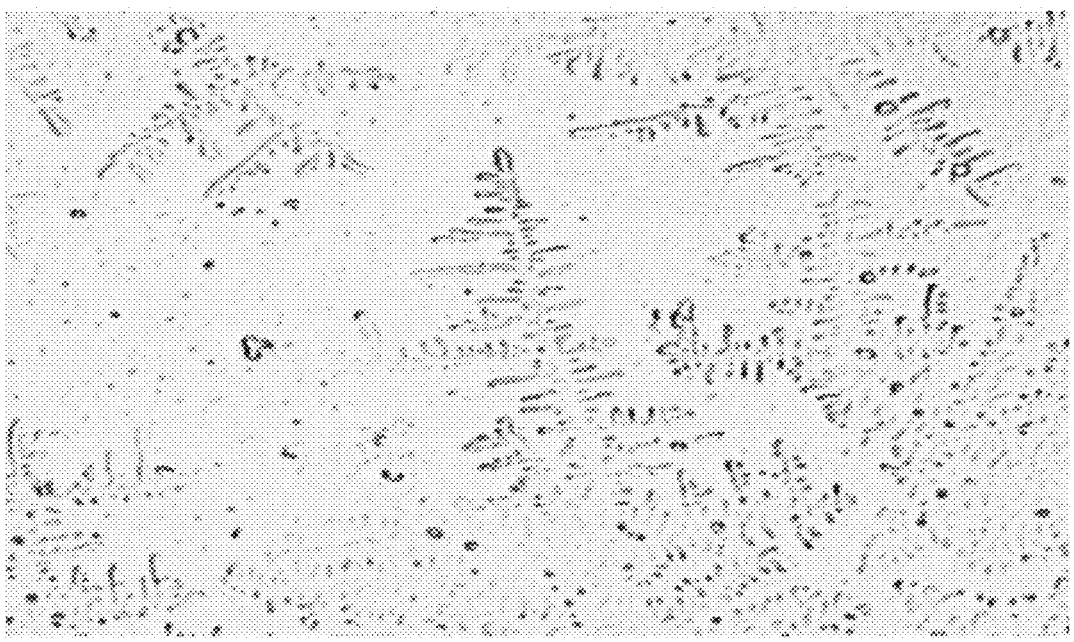

A ruler was placed by the side of the collection tube and the length of each mucus string was measured before breaking, as shown in FIG. 1D. This measurement corresponded to the stretchability or Spinnbarkeit of the mucilaginous extract. The extraction efficiency of the mucus was based on the amount of mucus recovered relative to the amount of HTF-bicarb used to extract the okra mucilage and did not differ significantly among preparations (30-36%). The Spinnbarkeit (stretchability) was similar among preparations (greater than 19 cm). The ferning pattern of mucilaginous extract was similar among preparations and mirrors the pattern observed in the follicular phase of the menstrual cycle (see FIGS. 2A-2B). The mucilaginous extract was stored at −80° C. for 5 weeks and longer.

J. Example 2: Sperm Penetration Test Using Mucilaginous Extract

The sperm penetration test protocol used in this application is a modification of the method of Tang et al. (1999), supra. Unless otherwise specified, all media were pre-equilibrated to 37° C. Non-treated Kimble circular cross-section capillary tubes, 75 mm in length and inner diameter 1.1 mm (Fisher Scientific, PA) were used. Each tube was filled by aspiration using a 1 mL tuberculin syringe and a plastic tube attached to the upper end of the capillary while the lower end was dipped into the *A. esculentus* mucus (100 µL) or equivalent volume of control medium (bicarbonate-buffered HTF containing 5% human serum albumin). An approximately 6.0 cm column of *A. esculentus* mucus or control medium was aspirated into the tube so that the upper meniscus was 1-2 cm from the top of the tube, while being careful not to trap air bubbles within the column. The top of each tube was sealed with modeling clay, such as PLASTI-CINE, and any trailing medium was cut off the lower end to produce a flat interface. Approximately 100 µl of liquefied semen was placed in the bottom of a small conical plastic tube and a capillary tube containing *A. esculentus* mucus or control medium placed with its open end in the semen. This preparation was replicated five times with semen samples from different donors. The two semen reservoirs and capillary tubes were mounted on a microscope slide as demonstrated in the WHO manual (WHO, 1999). The slides were then placed in a Petri dish and incubated in the horizontal position for 60 minutes at 37° C. in an atmosphere of 5% $CO_2$ in humidified air.

After 1 h, the motility of the spermatozoa was determined for the control and the mucilaginous extract sample by viewing the capillary tubes with a phase-contrast microscope at 200× magnification. A significant mean number of spermatozoa (>25±3 spermatozoa under 200× magnification) penetrated the mucilaginous extract and traveled approximately 45 mm (migration distance) within 1 h of initiation of interaction with semen versus 10±4 spermatozoa in the control preparation.

Figure 5A:
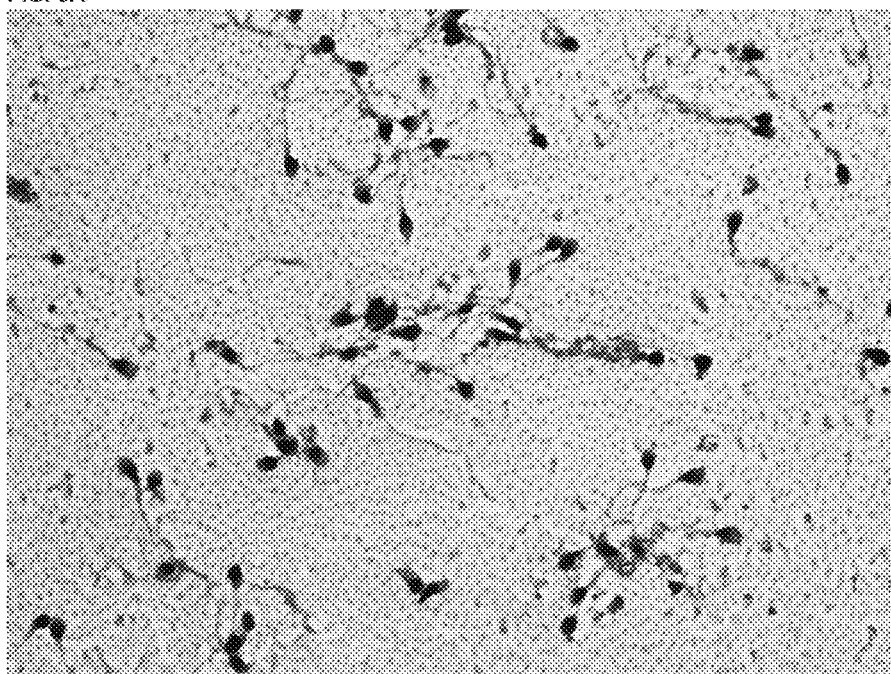
FIGS. 5A-5B: lack of penetration of mucilaginous extract by spermatozoa from semen of an infertility patient.
Figure 5B:
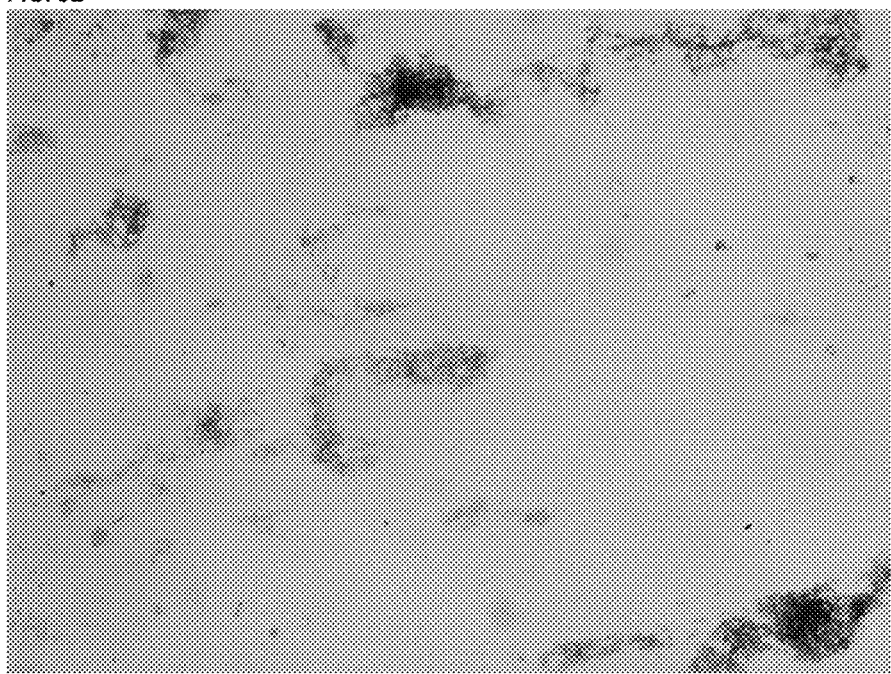
Figure 6A:
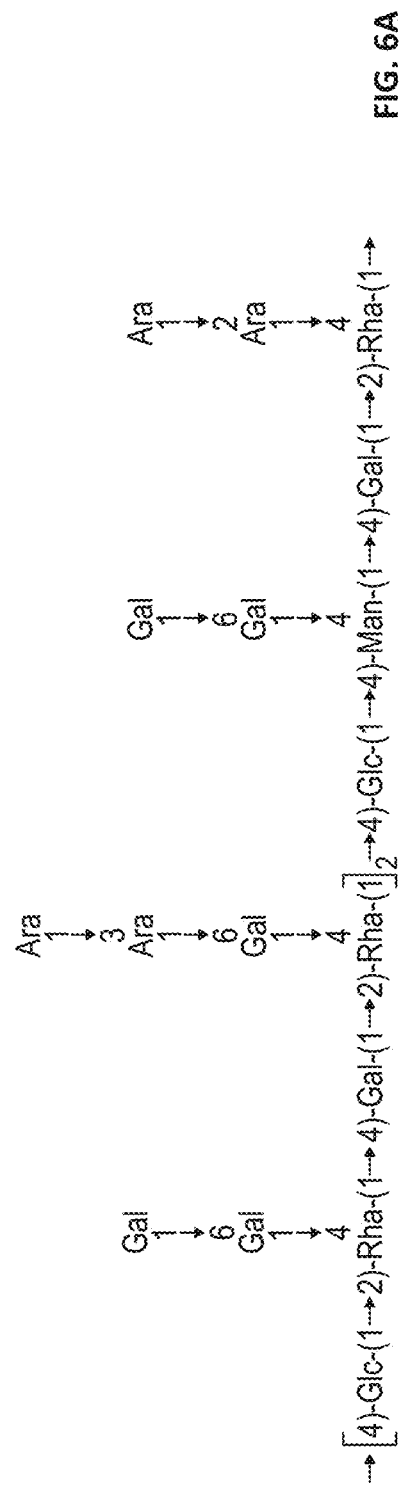
FIGS. 6A-6D: proposed structures of polysaccharides present in the extract. The degree of substitution and the length of side chains may vary among the individual fractions. Ara=arabinose; Gal=galactose; GalUA=galacturonic acid; Glc=glucose; GlcUA=glucuronic acid; Man=mannose; Rha=rhamnose.
Figure 6B:
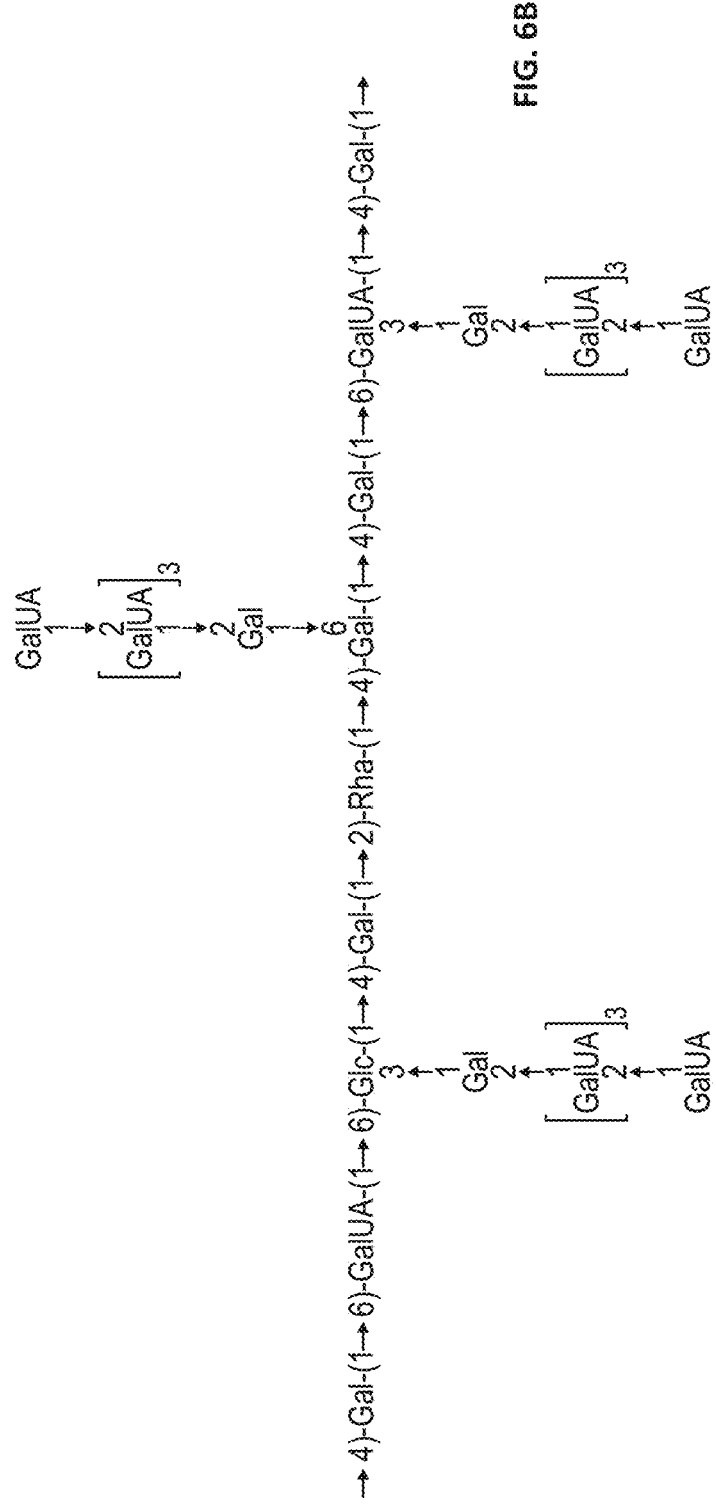
Figure 6C:
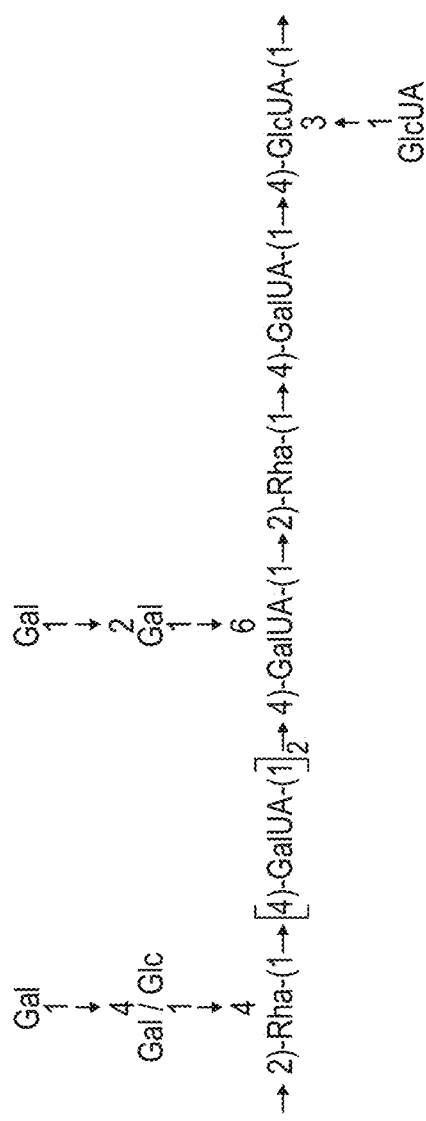
Figure 6D:
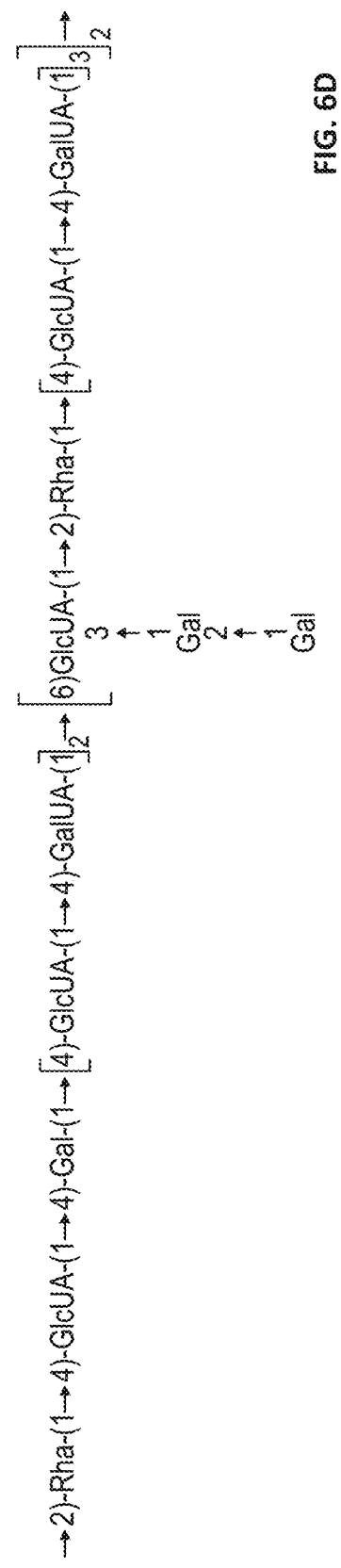

Determination of Progressive Motility of Recovered Human Spermatozoa in Mucilaginous Extract Approximately 10 µL of separated motile spermatozoa in mucilaginous extract was withdrawn from each capillary tube diluted in 190 µL of human tubal fluid (HTF) medium containing 0.5% human serum albumin (HSA) and 20 mM HEPES (HTF-HEPES; pH, 7.4), and a drop of the resulting solution was placed on a microscope slide. The percentage sperm motility was quantified manually with a phase-contrast microscope. Spermatozoa were considered to be progressively motile if they moved in a linear manner from one point to another. The percentage of progressively motile spermatozoa was determined twice for each sample by a certified clinical andrologist on 100 cells in different fields, with a laboratory counter and averaged. Counts were accepted as accurate if each of the two counts did not differ by 10%. The grade of motion on a scale of 0 to 4 was determined subjectively. The grade and percentage progressive motility of mucilaginous extract-penetrated spermatozoa were 3.5-4.0 and 86.8%, respectively, compared with those of the control (2.5-3.0, 47.7%, respectively). The above procedure was carried out using the sperm from patients (N=5) undergoing fertility evaluation to determine whether their spermatozoa would penetrate the mucilaginous extract. FIG. 5 shows that the spermatozoa from an infertile patient that did not penetrate the mucilaginous extract. These data suggest that mucilaginous extract can substitute for CF for testing sperm function.

Figure 3A:
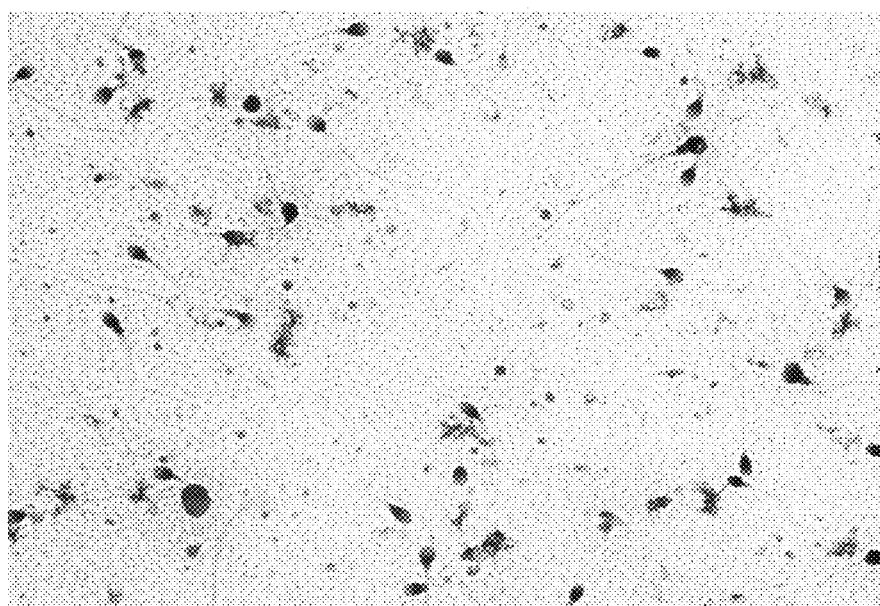
FIGS. 3A-3B: comparison of the morphology of spermatozoa in the semen control (FIG. 3A) and in the mucilaginous extract (FIG. 3B).
Figure 3B:
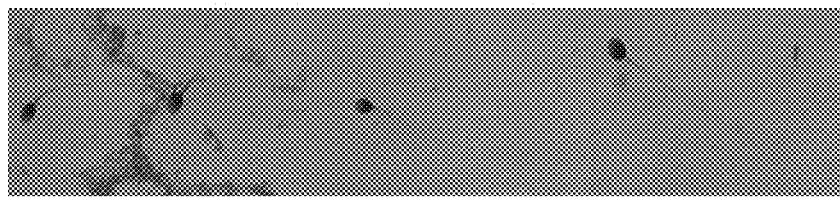
Figure 4:
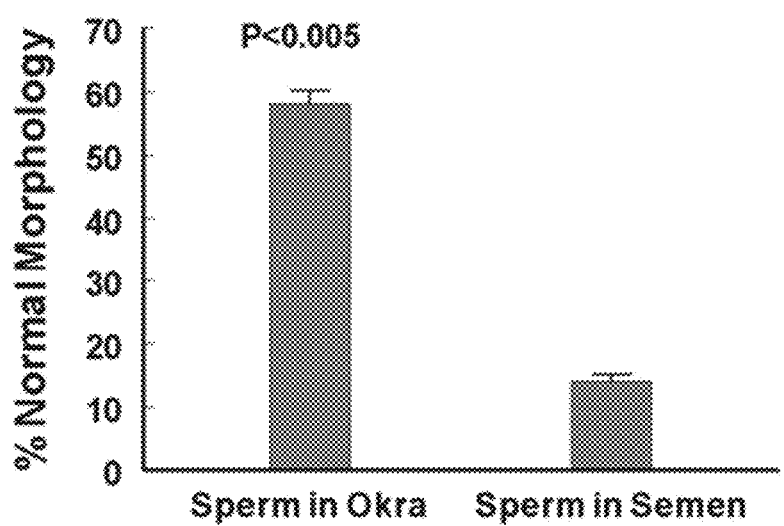
FIG. 4: percentage of normal morphological spermatozoa in mucilaginous extract vs. semen control.

Determination of Morphology of Recovered Human Spermatozoa in Mucilaginous Extract Sperm morphology assessment of spermatozoa in mucilaginous extract was conducted by a certified clinical andrologist. Feathered smears of approximately 10 µL each of undiluted mucilaginous extract containing human spermatozoa and matching semen (control; N=5/group) were prepared on ethanol-cleaned glass slides and left to dry in a dust-free chamber. Subsequently, smears were fixed and stained with reagents in a modified Papanicolaou staining kit (Spermac, Stain Enterprises, South Africa) according to the manufacturer's instructions and sperm morphologies assessed using the Kruger strict criteria with a phase-contrast microscope equipped with a scaler. A spermatozoon was considered normal if the head had a smooth, oval shape with a well-defined acrosome comprising approximately 40-70% of the head area. Morphologically, the sperm head must be 5.0-6.0 µM long and 2.5-3.5 µM wide to be considered normal. In addition, a spermatozoon was considered normal if it was devoid of neck, midpiece, or tail defects and no cytoplasmic droplet of more than half the size of the head. All borderline morphologic forms of spermatozoa were considered abnormal. The slides are shown in FIG. 3. The mean percentage of normal morphological form of spermatozoa in the mucilaginous extract samples is much greater than in the semen sample (control; see FIG. 4).

K. Example 3: Sperm Longevity and Viability after Thawing

Methods

Okra mucus extraction: Fresh okra was purchased from local grocery stores and mucus was extracted as described above.

Semen and processing: Discarded de-identified semen samples that met the criteria of WHO for normal semen samples (1.5-5.0 mL volume, 7.2-8.2 pH, 40% or greater motility, concentration=20×10 million/mL) were used in the freezing protocol with okra mucus. Each semen sample was divided into halves to be frozen in conventional freezing medium consisting of TEST Yolk Buffer containing 12% glycerol (volume/volume) and 10 µg gentamicin/ml (Irvine Scientific, Santa Ana, CA) or in the presence of okra mucus. Each half of semen samples designated for freezing in the presence of okra mucus was diluted with equivalent volume of human tubal fluid (HTF) buffer containing 25 mM sodium bicarbonate (HTF-buffer) and 25% okra mucus (volume/volume) from a 30% okra extract. The remaining half was similarly diluted with HTF medium only. Subsequently, an equivalent volume of TEST-Yolk buffer to each diluted semen sample was added dropwise with gentle mixing to a homogenous suspension with a final glycerol concentration of 6.0% (volume/volume), final okra dilution in ready to freeze preparation=12.5% (volume/volume of the 30% extract) and placed on ice for approximately 15 hours. Prior to subjecting each sample to freezing conditions, 10 µL of cooled TEST-Yolk-extended semen sample was withdrawn and placed on a clean glass slide, covered with cover glass and allowed to warm to room temperature (37° C.) before post-cooling evaluation of percentage sperm motility was conducted with a phase-contrast microscope and a laboratory counter. Cooled TEST-Yolk-extended semen samples were then subjected to liquid nitrogen (LN) vapor phase freezing for 30 minutes and subsequently stored immersed in LN. Samples were allowed to remain in LN storage for at least 24 hours before thawing. Samples were thawed to room temperature and subsequently diluted with two volumes of warm (37° C.) HTF-buffer in order to elute the cell-penetrating cryoprotectant (glycerol) from the cytoplasm of the cryopreserved spermatozoa. Frozen-thawed human spermatozoa were subjected to phase-contrast microscopy to determine the motility status of each sample as described above.

Acrosomal Status of Post-thaw Motile Spermatozoa and Longevity: After the assessment of post-thaw sperm motility, control and okra mucus-exposed samples subjected to gradient (ISOLATE, Irvine Scientific; 80%) centrifugation to separate motile from non-motile spermatozoa. Subsequently, motile spermatozoa were permeabilized in cold (−20° C.) 90% ethanol and stained with FITC-conjugated lectin (Vector Labs, Burlingame, CA). Following FITC-lectin staining, spermatozoa were subjected to epi-fluorescence microscopy. Spermatozoa with green even fluorescence in the acrosomal region were considered acrosome intact and therefore to lack damage to the membrane. Spermatozoa with fluorescence in the equatorial region of the cell were considered acrosome reacted and therefore to have sustained membrane damage.

Longevity of Non-frozen Human Spermatozoa in Okra Mucus: Liquefied freshly ejaculated human semen samples were washed with HTF containing 20 mM HEPES and 0.5% BSA (HTF-HEPES; pH 7.4) following which each sperm suspension was subjected to a continuous gradient wash as described above for the purpose of harvesting highly motile cells. Each sample of highly motile cells was divided into two to be cultured in HTF-buffer or HTF-buffer+25% okra mucus (volume [30% okra mucus in HTF-buffer]/volume [HTF-buffer]) for 18 hours in an atmosphere of 5% $CO_2$ in air in a humidified incubator.

Results

Figure 7:
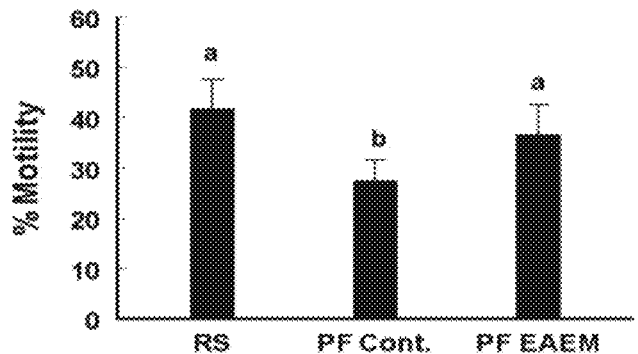
FIG. 7: sperm motility during slow cooling in okra mucus.
Figure 8:
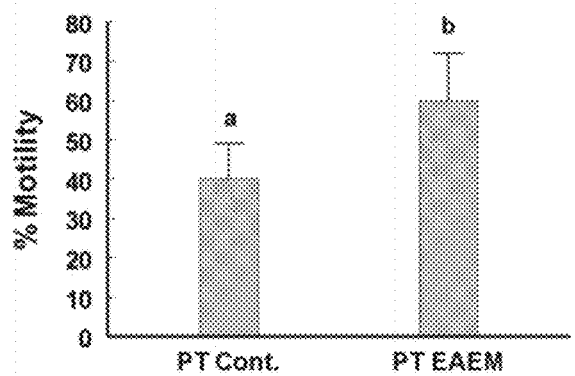
FIG. 8: post-thaw sperm motility in okra mucus.
Figure 9:
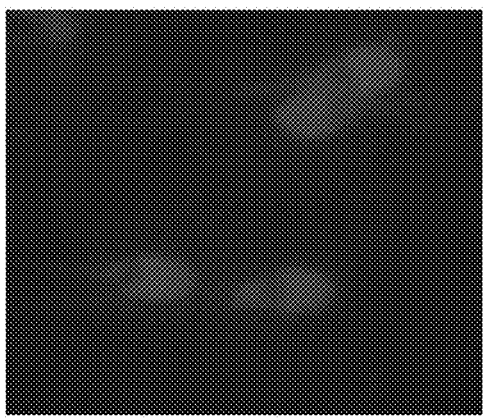
FIG. 9: acrosomal status/membrane integrity of frozen-thawed human spermatozoa.

During the pre-freezing period (PF), cooled spermatozoa in the base freezing buffer (control; PF control; FB) sustained a significant reduction in mean percentage motility ($p<0.02$) compared with those in cooled base freezing buffer supplemented with okra mucus (PF OK) or those in raw semen (RS). Further, supplementation of base freezing buffer with okra mucilage maintained a similar percentage motility rate observed in RS. (Graphs with different superscripts are statistically different; FIG. 7; graphs with different superscripts are statistically different). Freezing human semen in extracted *Abelmoschus esculentus* mucilage (EAEM) increased the percentage of post-thaw motile sperm population compared with FB ($P<0.03$; FIG. 8; graphs with different superscripts are statistically different). FIG. 9 shows a micrographic image of the frozen-thawed spermatozoa.

This observation suggests that more post-thaw motile spermatozoa can be harvested after freezing in EAEM for increased efficacy of affordable assisted reproductive technologies (ART) such as intrauterine insemination (IUI). Interestingly, spermatozoa in semen samples frozen in EAEM had a higher ($P<0.05$) percentage motility (35.3+3.4%) compared with those frozen in FB (23.5+4.1%), 8 hr post-thaw.

Regardless of the freezing medium, the highly motile spermatozoa harvested via gradient centrifugation maintained their membrane integrity. This suggests that if more motile spermatozoa are harvested based on higher percentage motility observed among cells frozen in EAEM, freezing in EAEM can facilitate the collection of a significant number of motile spermatozoa.

Figure 10:
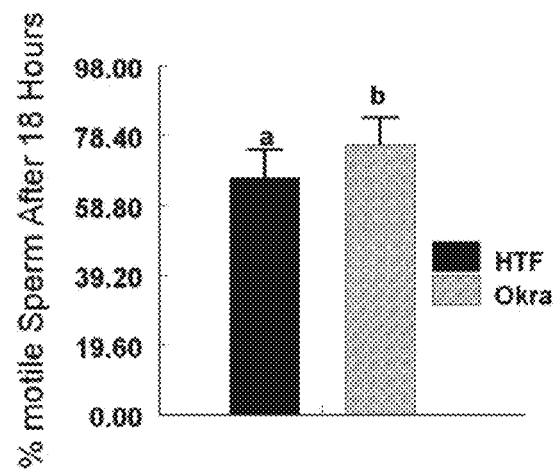
FIG. 10: enhanced longevity of human spermatozoa in HTF supplemented with okra mucus.

Highly motile spermatozoa (92.4±8%) harvested via continuous gradient centrifugation that were cultured for 18 hours in HTF-buffer supplemented with okra mucus had a higher percentage of motile spermatozoa ($P<0.05$; FIG. 10) than their counterparts cultured in HTF-buffer-only (graphs with different superscripts are statistically different). The result of this experiment indicates that culturing spermatozoa in the presence of okra mucus protects more spermatozoa to remain motile during a protracted period. The ability of okra mucus to maintain longevity in more cells than their counterparts cultured in HTF-only indicates that it has the potential to maintain more cells in motile state in women with a compromised cervix.

L. Example 4: Human Sperm/Okra Mucus Penetration Test

A test was conducted to determine whether okra mucilage functions as an effective medium to measure sperm penetration. Microscope slides were cleaned with 70% ethanol and thoroughly wiped dry with a task wipe. Subsequently, double-sided tape was applied to the clean glass slide, leaving a longitudinal strip uncovered approximately 50×2 mm (the "sperm lawn"). This was followed by the application of cover glass and pressed gently to eliminate air bubbles and firmly secure the cover glass. Thereafter, okra mucus extracted as described above was applied steadily to the 10° angled uncovered side of the glass slide to permit the mucus to penetrate the sperm lawn without air bubbles. The mucus loaded slide was placed in a 100×20 mm FALCON style polystyrene nonpyrogenic Petri dish (Corning, Inc., Corning, NY) and placed in a humidified incubator with an atmosphere of 37° C. and 5.0% $CO_2$ for about 45 minutes for the mucus to attain zero movement (acquire static status). Subsequently, 10 μL of semen was carefully placed in the okra mucus, just before the edge of the cover glass and incubated as described above for 30 minutes. Post incubation, the preparation was subjected to phase-contrast microscopy at a magnification of 200× for sperm penetration of the mucus, phalange (finger-like projections of the seminal fluid into the okra mucus creating an interface between the two substances) formation and distance traveled down the sperm lawn from the loading zone.

All preparations developed phalanges. However, spermatozoa in semen samples (N=5) that did not meet the WHO criteria for normalcy had zero to poor transition and travelling distance (mean=1.75±0.8 cm) with the number of motile spermatozoa in first microscopic field (F1) from the tip of a phalange showing 7 cells, F2 showing 10 cells, and F3 showing 9 cells. Spermatozoa in semen that met the WHO criteria for normalcy were superior ($P<0.05$) in their transition and travel distance in the sperm lawn. The mean distance traveled by spermatozoa in normal samples (N=7) was 4.23±0.05 cm in 30 minutes. The F1, F2, and F3 for spermatozoa in normal semen samples were 48 cells, 45 cells, and 39 cells, respectively.

Implications: The observations made in this study indicate that the preparation described above has the potential to be utilized as a replacement cervical mucus kit. Okra mucus-loaded slides as described above can be prepared and snap frozen and used when needed by thawing in a humidified chamber as described above followed by semen application, incubation as described above and evaluated for phalange formations, transition of spermatozoa into okra mucus, evaluation of the number of motile spermatozoa in microscopic fields from the phalanges and distance traveled.

M. Example 5: Method of Making Okra-Derived Composition

Figure 12A:
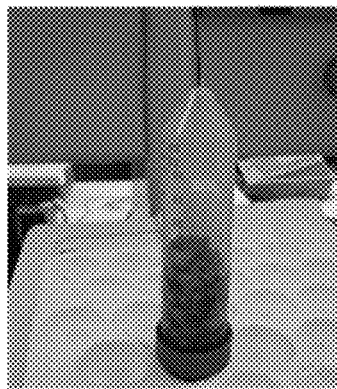
FIGS. 12A-12D: extraction of the okra fruits.
Figure 12B:
Figure 12C:
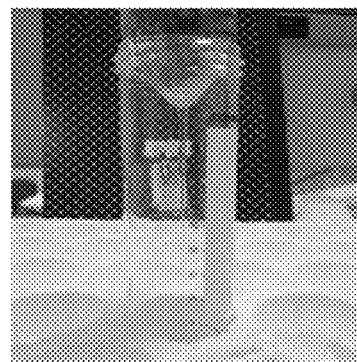

An 8"×8" aluminum sheet was sterilized with 70% ethanol and wiped dry with a task wipe, such as KIMWIPES. Six okra fruits were thoroughly washed with a mild soap solution prior to being thoroughly rinsed five times with 500 mL tap water (each rinse). Subsequently, the okra fruits were rinsed as described above with de-ionized water prior to being place in a 2 liter Pyrex dish to which Sterile Dulbecco Phosphate Buffered Saline (DPBS) containing 0.69 g penicillin/l and 0.5 g streptocysin/l was added to cover the okra fruits and rocked on a rocker platform for 6 hours. The okra fruits were washed with deionized water and dried as described above. The okra fruits were then placed on sterile aluminum foil and sliced into 1-2 mm okra sections with a sterile scalpel blade. Aliquots of 11.25 g sliced okra fruit portions were each placed in a 50 ml centrifuge tube and subjected to 30% extraction with 37.5 ml DPBS containing 0.6 mg penicillin and 0.5 mg streptomycin/ml. Extraction tubes were rocked at 4° C. on a tissue rocker/shaker for 4 hours. Each extraction centrifuge tube was inverted and the bottom sterilized with 70% ethanol wipe. Using a pre-heated 18G needle, a pinhole was created at the center of the bottom of the tube with a pore size of approximately 1.0 mm (large enough to permit fluid escape but small enough to prevent okra seed escape—FIG. 12A). Each extraction tube was inverted over another uncapped 50 ml centrifuge tube (FIG. 12B). The cap to the extraction tube was loosened to permit the clear extracted okra mucus to drip under gravitational force into the collection tube (FIG. 12C).

Figure 12D:
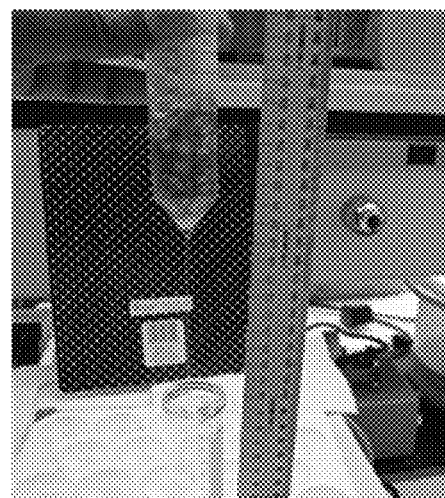

A ruler was placed by the side of the collection tube and the length of each mucus string was measured before breaking, as shown in FIG. 12D. This measurement corresponded to the stretchability or Spinnbarkeit of the okra composition. Ferning was conducted to establish similarity of the DPBS extract with cervical mucus by preparing feathered smears of okra extract from each preparation on 70% ethanol cleansed microscope slides and dried overnight in a dust-free chamber. The extracted mucus was clear and devoid of chlorophyll pigment. The Spinnbarkeit (stretchability) was similar among preparations and was >15-19 cm. The ferning pattern of extracted okra mucilage in DPBS mirrored the pattern observed in the follicular phase of the menstrual cycle.

N. Example 6: Okra-Derived Composition Blocks HIV-1 Transcytosis

Materials and Methods

To test whether the okra composition has the potential to block HIV transmission, VK2/E6E7 cells, a human vaginal cell line, were pre-treated with concentrations of ½ diluted okra composition, ¼ diluted okra composition, and ⅛ diluted okra composition for 1 hour. Subsequently, HIV-1 IIIB virus (60 ng p24 content) was added to the VK2/E6E7 cells for 4 hours, following which, 0.03% Trypsin was used to remove the HIV particles attached to the surface of the cells (outside the cells). After washing three times with PBS, the cells were subjected to Western-blot analysis. The antigen targeted and detected in the Western-blot was HIV-1 capsid protein p24.

Results

Figure 13:
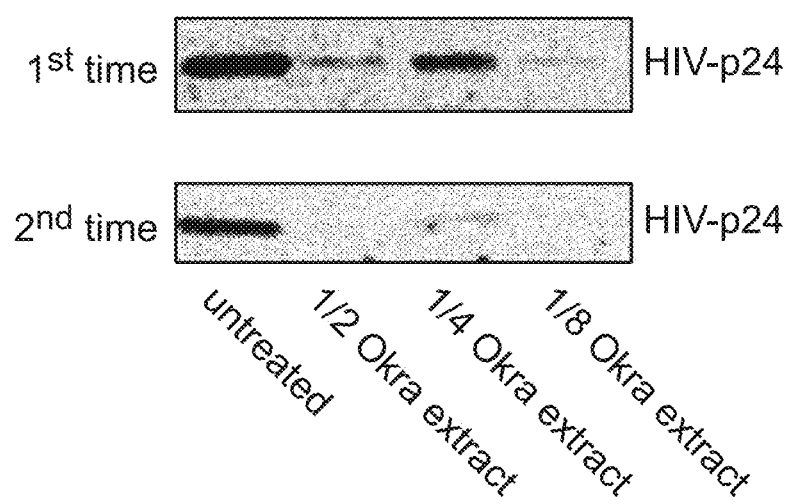
FIG. 13: Western-blot analysis showing that the okra composition inhibits the accumulation of HIV in VK2/E6E7 cells.

As shown in FIG. 13, the okra composition dramatically reduced the amount of HIV in the cells. As can be seen, all concentrations of the okra composition nearly completely inhibited the accumulation of HIV inside the VK2/E6E7 cells. These data demonstrate that the okra composition is able to block the transcytosis of HIV through vaginal epithelial cells and suggest that the okra composition has the potential for development as an anti-HIV/AIDS agent.

O. Example 7: Okra-Derived Composition Inhibits HIV Replication in CD4+ T Cells Materials and Methods CD4+ T cells are the primary cell type supporting HIV replication. In order to evaluate the inhibitory effect of the okra composition on HIV replication, SupT1 cells, a human T cell lymphoblastic Lymphoma cell line, were pre-treated with concentrations of ½ diluted okra composition, ¼ diluted okra composition, and ⅛ diluted okra composition for 1 hour. Subsequently, HIV IIIB (60 ng p24 content) was added to the cell culture to infect the SupT1 cells for 4 hours, following which, the cells were washed three times with PBS. The SupT1 cells were then subjected to in vitro cell culture for eight days. Aliquots of conditioned media were harvested on each of day 0, 2, 4, 6, and 8 and subjected to qRT-PCR to measure viral release. The target sequence for the qRT-PCR was in the HIV-1 LTR region.

Results

Figure 14A:
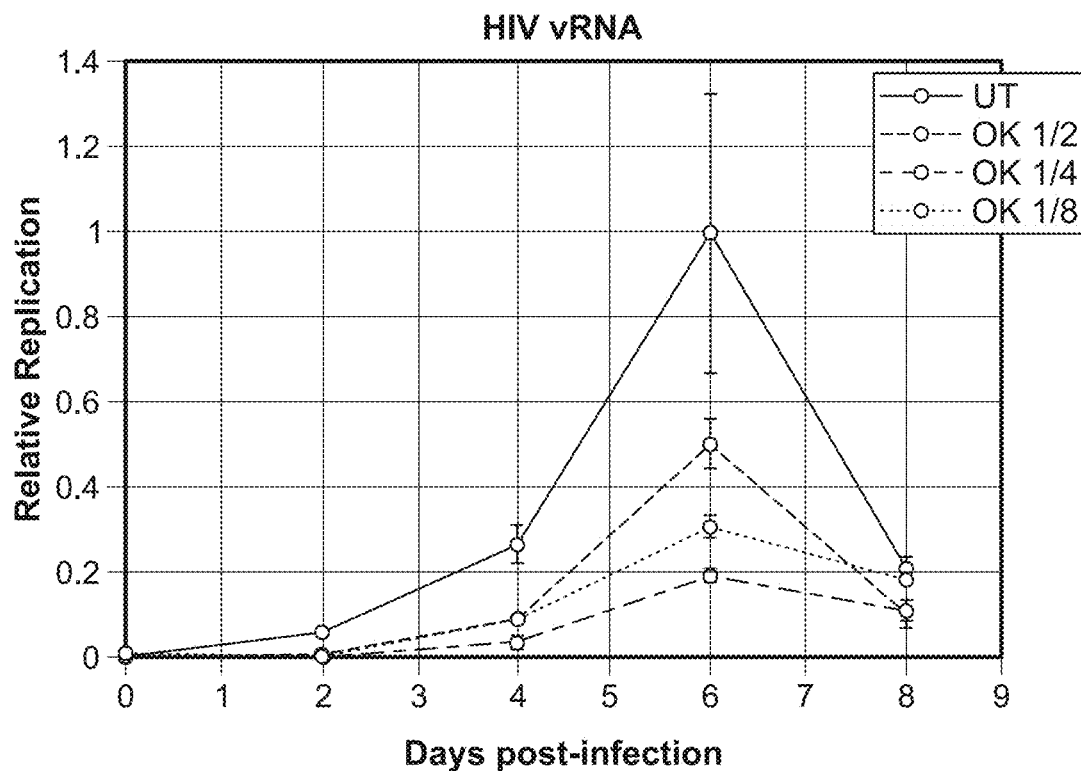
FIG. 14A: graph showing that the okra composition inhibits viral replication in CD4+ T cells.
Figure 14B:
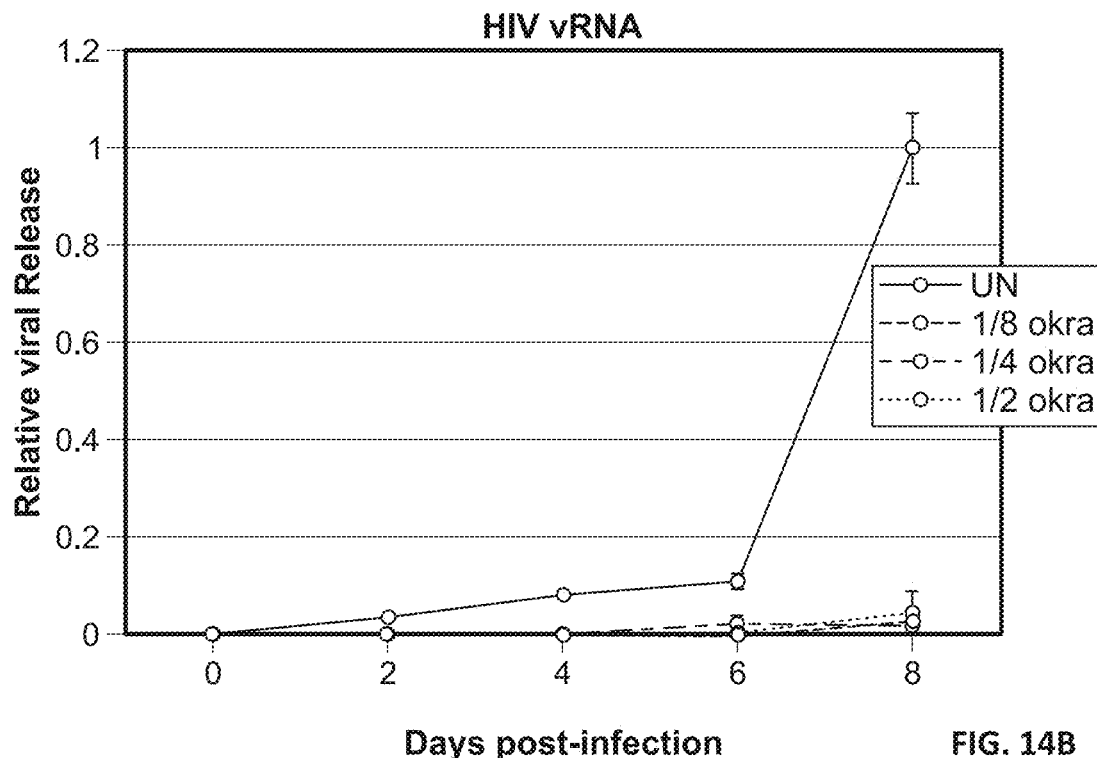
FIG. 14B: graph showing that the okra composition inhibits viral release in CD4+ T cells.

As shown in FIGS. 14A and 14B, the okra composition dramatically inhibited HIV replication (FIG. 14A) and viral release (FIG. 14B) in SupT1 cells. These results indicate that the okra composition not only inhibits HIV transmission in vaginal epithelial cells, but also inhibits viral replication in CD4+ T cells.

P. Example 8: Okra-Derived Composition is not Toxic to Supt1 Cells

Materials and Methods

To test the cytotoxicity of the okra composition on SupT1 cells, ¼ diluted okra composition was used to treat SupT1 cells for 5 hours. After treatment, the SupT1 cells were subjected to a cell viability assay using LIVE/DEAD® Cell Vitality Assay Kit (Invitrogen).

Results

Figure 15:
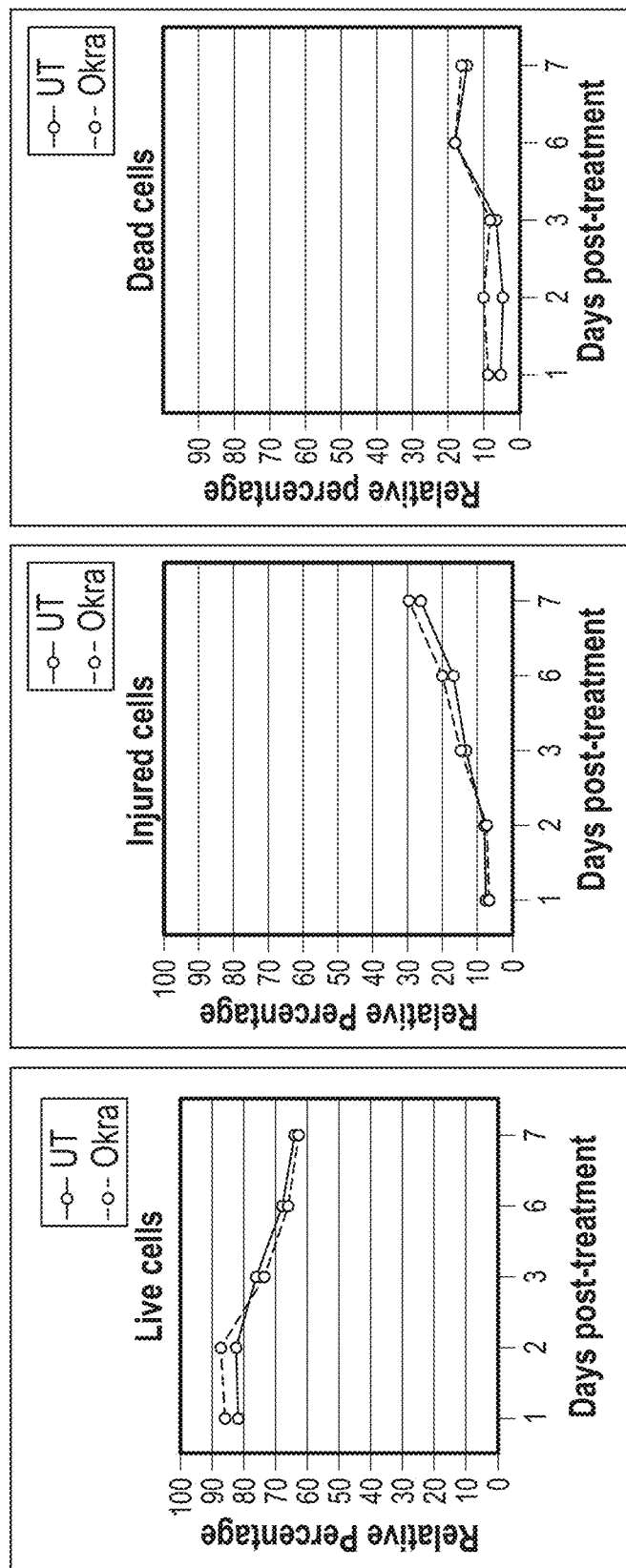
FIG. 15: graphs showing that the okra composition is not toxic to SupT1 cells.

As shown in the graphs of FIG. 15, the okra composition did not alter the viability of SupT1 cells.

Q. Conclusions

It is to be understood that any given element(s) of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed:

1. A method of decreasing the endocytosis of a virus into a eukaryotic cell, the method comprising:
    contacting the eukaryotic cell with an okra-derived composition in the presence of the virus, wherein the okra-derived composition is a product by process of extracting a fruit of okra and separating a substantially clear fluid from the extract;
    wherein the eukaryotic cell is selected from the group consisting of dendritic cell, T cell, vaginal epithelial cell, cervical epithelial cell, uterine epithelial cell, and rectal epithelial cell, and
    wherein the virus is selected from the group consisting of herpes simplex viruses, human papillomavirus, human immunodeficiency virus, hepatitis B virus and cytomegalovirus.

2. The method of claim 1, wherein the eukaryotic cell is a vaginal epithelial cell.

3. The method of claim 1, wherein the virus is human immunodeficiency virus.

4. The method of claim 1, wherein the okra-derived composition is a product by process of (a) extracting a fruit of okra in an aqueous medium, to produce a first extract; (b) separating a substantially clear fluid from the first extract; and (c) straining the first extract through one or more pores having an effective pore size of about 1 mm or less.

5. The method of claim 4, wherein the aqueous medium comprises bicarbonate-buffered human tubal fluid.

6. The method of claim 4, wherein the aqueous medium comprises bicarbonate-buffered human tubal fluid and mammalian serum albumin.

7. The method of claim 4, wherein the aqueous medium comprises an antibiotic selected from the group consisting of penicillin, streptomycin, and a combination thereof.

8. The method of claim 1, wherein the step of extracting further comprises boiling the fruit of okra in the aqueous medium.

9. The method of claim 1, wherein the step of extracting further comprises contacting the fruit of okra with the aqueous medium at a temperature of about 4° C. for about 4 hours.

10. The method of claim 1, wherein the eukaryotic cell is a T cell.

* * * * *